(12) United States Patent
Lineaweaver et al.

(10) Patent No.: US 8,255,059 B2
(45) Date of Patent: Aug. 28, 2012

(54) USING A GENETIC ALGORITHM TO FIT A MEDICAL IMPLANT SYSTEM TO A PATIENT

(75) Inventors: Sean Lineaweaver, Parker, CO (US); Gregory H. Wakefield, Ann Arbor, MI (US)

(73) Assignee: Cochlear Limited, Macquarie University, NSW (AU)

( * ) Notice: Subject to any disclaimer, the term of this patent is extended or adjusted under 35 U.S.C. 154(b) by 276 days.

(21) Appl. No.: 12/557,208

(22) Filed: Sep. 10, 2009

(65) Prior Publication Data
US 2010/0152813 A1    Jun. 17, 2010

Related U.S. Application Data

(63) Continuation-in-part of application No. 10/963,594, filed on Oct. 14, 2004, which is a continuation-in-part of application No. 10/385,880, filed on Mar. 11, 2003, now Pat. No. 6,879,860.

(51) Int. Cl.
*A61N 1/00* (2006.01)
(52) U.S. Cl. ........................................ 607/57
(58) Field of Classification Search .............. 607/55–57, 607/59, 2
See application file for complete search history.

(56) References Cited

U.S. PATENT DOCUMENTS

| | | | |
|---|---|---|---|
| 4,532,930 A | 8/1985 | Crosby et al. | |
| 4,953,112 A | 8/1990 | Widin et al. | |
| 5,095,904 A | 3/1992 | Seligman et al. | |
| 5,277,694 A | 1/1994 | Leysieffer et al. | |
| 5,626,629 A | 5/1997 | Faltys et al. | |
| 6,157,861 A | 12/2000 | Faltys et al. | |
| 6,697,674 B2 | 2/2004 | Leysieffer | |
| 7,343,021 B2 | 3/2008 | Takagi et al. | |
| 2002/0176584 A1 | 11/2002 | Kates | |
| 2003/0133578 A1 | 7/2003 | Durant | |
| 2005/0107845 A1 | 5/2005 | Wakefield et al. | |
| 2005/0129262 A1 | 6/2005 | Dillon et al. | |
| 2008/0165978 A1 | 7/2008 | Cronin et al. | |
| 2010/0280307 A1 | 11/2010 | Lineaweaver et al. | |
| 2011/0060383 A1 | 3/2011 | Lineaweaver et al. | |
| 2011/0060702 A1 | 3/2011 | Lineaweaver | |

FOREIGN PATENT DOCUMENTS

| | | |
|---|---|---|
| JP | 09-325773 | 12/1997 |
| JP | 11-513539 | 11/1999 |
| JP | 2003-6171 | 1/2003 |
| WO | WO 2007/090243 | 8/2007 |

OTHER PUBLICATIONS

International Search Report for PCT/US04/07400 mailed Aug. 27, 2004.
Written Opinion for PCT/US04/07400 dated Aug. 27, 2004.

(Continued)

*Primary Examiner* — Scott Getzow
(74) *Attorney, Agent, or Firm* — Kilpatrick, Townsend & Stockton, LLP.

(57) ABSTRACT

Apparatus and method for at least partially fitting a medical implant system to a patient is described. These apparatuses and methods comprise executing a genetic algorithm to select a set of parameter values for the medical implant system. This genetic algorithm may comprise executing a tabu search wherein value sets that are determined to be bad are added to a tabu list that may be consulted to exclude tabu value sets from successive generations of the genetic algorithm.

50 Claims, 13 Drawing Sheets

OTHER PUBLICATIONS

Forrest, Stephanie, "Genetic Algorithms: Principles of Natural Selection Applied to Computation," Science, Aug. 13, 1993, vol. 261 (5123), pp. 872-878.

Takagi, Hideyuki, "Interactive Evolutionary Computation: Fusion of the Capabilities of EC Optimization and Human Evaluation," Proceedings of the IEEE, Sep. 2001, vol. 89, No. 9, pp. 1275-1296.

Hideyuki Takagi, IEC-based Hearing Aid Fitting, IEEE SM C' 99 Conference Proceedings, Oct. 1999, vol. 3, 657-662 (6 pages).

International Search Report for International Application No. PCT/IB2010/054105 mailed Jun. 14, 2011 (5 pages).

European Official Communication for European Application No. 04 719 779.3 mailed Apr. 20, 2011 (3 pages).

Canadian Intellectual Property Office, "Office Action," issued in connection with Canadian Patent Application Serial No. 2,518,997, on Apr. 16, 2010 (2 pages).

Skinner, et al., "Speech Recognition with the Nucleus 24 SPEAK, ACE, and CIS Speech Coding Strategies in newly Implanted Adults," Ear & Hearing, vol. 23, No. 3, 208-223, (Jun. 2002) (17 pages).

Skinner, et al., "Nucleus 24 Advanced Encoder Conversion Study: Performance versus Preference," Ear & Hearing, vol. 23, No. 18, 3S-7S, (Feb. 2002) (16 pages).

Wakefield, et al., "Recipient-Directed Design of Speech processor MAPs," in R.T. Miyamoto, ed., Cochlear Implants, Elsevier, International Congress Series, 1273 178-182 (2004) (5 pages).

Wakefield, et al., "Genetic Algorithms for Adaptive Psychopysical Procedures: Recipient-Directed Design of Speech-Processor MAPs," Ear & Hearing, 52S-72S, (Aug. 2005) (16 pages).

Japanese Office Action for Japanese Application No. 2006-507068 mailed on Jun. 1, 2010 along with English translation (4 pages).

Japanese Office Action for Japanese Application No. 2006-507068 mailed on Mar. 8, 2011 along with English translation (3 pages).

Japanese Office Action for Japanese Application No. 2006-507068 mailed on Oct. 18, 2011 along with English translation (5 pages).

GENERATION N
EVOLUTION SEQUENCE

GENERATION N
SELECTION

GENERATION N SURVIVAL OF
THE FITTEST

PAIRS OF PARENTS
PROCREATE

GENERATION N + 1 OFFSPRING
FORM NEXT GENERATION

FIG. 6

| BIT STRING | MAP PARAMETERS ||||| 
|---|---|---|---|---|---|
| | RATE | # OF MAXIMA | # OF ELECTRODES | COMPRESSION (Q) | AUDIO FILTERING |
| 00000000 | 250 | 4 | 22 | 20 | FLAT |
| 00000001 | 250 | 6 | 22 | 20 | FLAT |
| 00000010 | 250 | 8 | 22 | 20 | FLAT |
| 00000011 | 720 | 6 | 22 | 20 | FLAT |
| 00000100 | 1200 | 6 | 22 | 20 | FLAT |
| 00000101 | 720 | 8 | 22 | 20 | FLAT |
| 00000110 | 250 | 12 | 22 | 20 | FLAT |
| 00000111 | 250 | 16 | 22 | 20 | FLAT |
| | 119 OTHER LEGAL COMBINATIONS OF RATE, # OF MAXIMA, # OF ELECTRODES, COMPRESSION Q, AND AUDIO FILTERING |||||
| 01111111 | 250 | 4 | 10 | 30 | HIGH CUT |
| 10000000 | 250 | 4 | 22 | 20 | LOW CUT |
| | 126 OTHER LEGAL COMBINATIONS OF RATE, # OF MAXIMA, # OF ELECTRODES, COMPRESSION Q, AND AUDIO FILTERING |||||
| 11111111 | 250 | 4 | 10 | 30 | HIGH CUT + LOW CUT |

FIG. 9

| NUMBER OF CHNL | STIM. RATE | NO. OF MAXIMA | Q | FAT SHIFT | T-LEVEL BUMP | FILTERS |
|---|---|---|---|---|---|---|
| 8 | 250 | 6 | 10 | DEFAULT SHIFT | DEFAULT BUMP | LOW B |
| 12 | 720 | 8 | 20 | | | LOW CUT |
| 20 | 900 | 12 | | | | HIGH CUT |
| | 1200 | 16 | | | | LOW C |
| | 1800 | 20 | | | | HIGH C |
| | 2400 | | | | | FLAT |

FIG. 10

| BINARY | NUMBER OF CHNL | STIM. RATE | NO. OF MAXIMA | Q | FAT SHIFT | T LEVEL | FILTERS |
|---|---|---|---|---|---|---|---|
| 0000000000 | 20 | 250 | 8 | 10 | 1 | 1 | 1 |
| 0000000001 | 20 | 250 | 8 | 10 | 1 | 1 | 2 |
| 0000000010 | 20 | 250 | 8 | 10 | 1 | 1 | 3 |

FIG. 11

| FREQ. INDEX | TABLE 6 | TABLE 7 | TABLE 8 | TABLE 14 | TABLE 15 | TABLE 16 |
|---|---|---|---|---|---|---|
| 0 | 188 | 188 | 188 | 188 | 188 | 188 |
| 1 | 313 | 313 | 313 | 313 | 313 | 313 |
| 2 | 438 | 438 | 438 | 563 | 563 | 563 |
| . | . | . | . | . | . | . |
| . | . | . | . | . | . | . |
| 10 | 1563 | 1688 | 1688 | 3438 | 4063 | 4813 |
| 11 | 1813 | 1938 | 1938 | 4188 | 5063 | 6188 |
| 12 | 2063 | 2188 | 2313 | 5188 | 6313 | 7938 |
| 13 | 2313 | 2563 | 2688 | 6313 | 7938 | |
| . | . | . | . | . | | |
| . | . | . | . | | | |
| . | . | . | . | | | |
| 20 | 6063 | 6938 | 7938 | | | |
| 21 | 6938 | 7938 | | | | |
| 22 | 7938 | | | | | |

USING A GENETIC ALGORITHM TO FIT A MEDICAL IMPLANT SYSTEM TO A PATIENT

CROSS-REFERENCE TO RELATED APPLICATIONS

This application is a continuation-in-part of and claims priority to U.S. patent application Ser. No. 10/963,594, entitled "Using a Genetic Algorithm to Fit a Cochlear implant System to a Patient," filed Oct. 13, 2004, which is a continuation-in-part of and claims priority to U.S. Pat. No. 6,879,860, entitled "Cochlear Implant Map Optimization With Use Of A Genetic Algorithm," filed Mar. 11, 2003, the entire contents and disclosures of each are hereby incorporated by reference.

This application is related to PCT Application No. PCT/US2004/007400, U.S. Pat. Nos. 4,532,930, 5,277,694, 6,123,660, 6,162,169, 6,537,200, 6,565,503, 6,575,894, 6,697,674, U.S. patent application Ser. No. 12/557,233, entitled "Using a Genetic Algorithm Employing an Expedited Convergence Algorithm," filed concurrent with the present application, and U.S. patent application Ser. No. 12/557,218, entitled "Using a Genetic Algorithm Employing Dynamic Mutation," filed concurrent with the present application. The entire disclosure and contents of the above patents are hereby incorporated by reference herein.

BACKGROUND

1. Field of the Invention

The present invention relates generally to genetic algorithms and, more particularly, to using a genetic algorithm to obtain a set of parameters for a device.

2. Related Art

Many medical devices have structural and/or functional features which are to be adjusted for an individual patient. The process by which a medical device is tailored or customized for the specific needs of a patient is commonly referred to as fitting. One type of medical device which is typically fitted to individual recipients is a cochlear implant system.

Cochlear implant systems provide the benefit of hearing to individuals suffering from severe to profound hearing loss. Hearing loss in such individuals is often due to the absence or destruction of the hair cells in the cochlea which transduce acoustic signals into nerve impulses. Cochlear implant systems essentially stimulate the auditory nerves by directly delivering electrical stimulation to the auditory nerve fibers. This causes the brain to perceive a hearing sensation resembling the natural hearing sensation normally delivered by the auditory nerve. Examples of cochlear implant systems are described, by way of example, in U.S. Pat. Nos. 4,532,930, 6,537,200, 6,565,503, 6,575,894, and 6,697,674, among others.

Conventional cochlear implant systems commonly include an external assembly directly or indirectly attached to the body of the patient (sometimes referred to herein as the recipient), and an internal assembly which is implanted in the patient. The external assembly typically comprises one or more microphones for detecting sound, a speech processing unit that converts detected sound into an electrical coded signal, a power source, and an external transcutaneous transfer coil. The internal assembly typically comprises an internal transcutaneous transfer coil, a stimulator unit located within a recess of the temporal bone of the recipient, and an electrode array positioned in the recipient's cochlea. Completely implantable cochlear implant systems having functionally similar components are under development.

In addition to providing electrical stimulation, some cochlear implant systems also include a mechanical stimulation mode of operation. Such so called mixed-mode systems offer rehabilitation by mechanically stimulating a portion of a patient's auditory pathway, either acoustically or physically. For example, there have been approaches to offer rehabilitation with conventional hearing aids via the application of an amplified acoustic signal to the external auditory canal, or by physically stimulating an ossicle of the middle ear or the inner ear via mechanical or hydromechanical stimulation.

Modern cochlear implant systems provide a wide variety of fitting options that can be customized for an individual patient. Because patients are heterogeneous, each patient requires a different set of parameters to maximize speech reception and patient satisfaction. The task of the clinical professional, usually an audiologist, is to select a set of parameters, commonly referred to as a parameter map or, more simply, a MAP that will provide the best possible sound reception for an individual patient. Because there may be thousands of possible parameter maps, it is impractical for a patient to experience all of the alternatives and to evaluate the performance of each alternative for an individual patient. Nor is it possible to identify an optimal parameter map by prescription based on a limited set of measurements as is, for example, the case in fitting eyeglasses. Because parameters of cochlear implant systems often interact non-linearly and non-monotonically, it is also not possible to sequentially optimize parameters one at a time, adjusting each in succession to its optimal value.

As a result, clinicians have adopted a variety of approaches for fitting the cochlear implant systems to a patient. Some simply set the parameters to default values regardless of the individual patients. Others adopt preferred parameter maps, which they believe are good, if not best, for many or most patients. The preferences may be based on personal experience, published performance data, or intuition. Some clinicians evaluate a limited set of alternatives adjusting individual parameters based upon measured perceptual limitations and inferred relationships among the parameters. These approaches are time consuming, costly, and unreliable, and typically fail to achieve the optimal outcome for individual patients.

SUMMARY

In one aspect of the invention, a method for at least partially fitting a medical implant system to a patient is provided. This method comprises executing a genetic algorithm to select a determined value set comprising values for a plurality of fitting parameters, the genetic algorithm comprising: presenting signals processed by a plurality of value sets to the patient using the medical implant system; receiving patient feedback in response to the presented signals processed by the plurality of value sets; selecting, based on the patient feedback, one or more of the value sets; storing information, based on patient feedback, regarding one or more value sets that are to be excluded; and generating one or more successive generations of value sets using said selected one or more value sets; wherein said stored information is used to exclude one or more value sets from said successive generations; and providing said determined value set to said medical implant system for use in providing stimulation to the patient.

In another aspect, a system for at least partially fitting a medical implant system to a patient is provided. This system comprises a processor configured to execute a genetic algorithm to select a determined value set comprising values for a plurality of fitting parameters, the genetic algorithm comprising: presenting signals processed by a plurality of value sets to the patient using the medical implant system, receiving patient feedback in response to the presented signals processed by the plurality of value sets, selecting, based on the patient feedback, one or more of the value sets, storing information, based on patient feedback, regarding one or more value sets that are to be excluded, and generating one or more successive generations of value sets using said selected one or more value sets, wherein said stored information is used to exclude one or more value sets from said successive generations; a storage configured to store the information regarding one or more value sets that are to be excluded; and an interface configured to provide at least one of the value sets to the medical implant system for use by the medical implant system in providing stimulation to the patient.

In yet another aspect, a system for at least partially fitting a medical implant system to a patient is provided. This system comprises means for executing a genetic algorithm to select a determined value set comprising values for a plurality of fitting parameters, the means for executing the genetic algorithm comprising: means for presenting signals processed by a plurality of value sets to the patient using the medical implant system; means for receiving patient feedback in response to the presented signals processed by the plurality of value sets; means for selecting, based on the patient feedback, one or more of the value sets; means for storing information, based on patient feedback, regarding one or more value sets that are to be excluded; and means for generating one or more successive generations of value sets using said selected one or more value sets; wherein said stored information is used to exclude one or more value sets from said successive generations; and means for providing said determined value set to said medical implant system for use in providing stimulation to the patient.

In yet another aspect, there is provided a computer-readable media encoded with instructions operative to cause a computer to perform a method for at least partially fitting a medical implant system to a patient. This method comprise: executing a genetic algorithm to select a determined value set comprising values for a plurality of fitting parameters, the genetic algorithm comprising: presenting signals processed by a plurality of value sets to the patient using the medical implant system; receiving patient feedback in response to the presented signals processed by the plurality of value sets; selecting, based on the patient feedback, one or more of the value sets; storing information, based on patient feedback, regarding one or more value sets that are to be excluded; and generating one or more successive generations of value sets using said selected one or more value sets; wherein said stored information is used to exclude one or more value sets from said successive generations; and providing said determined value set to said medical implant system for use in providing stimulation to the patient.

BRIEF DESCRIPTION OF THE DRAWINGS

FIG. 6 is a logical block diagram illustrating a manner in which a parameter map formed of a bit string represents parameter values, in accordance with an embodiment.

FIG. 9 is a table of seven parameters that can be determined using the subject algorithm, and the possible values of each parameter, in accordance with an embodiment.

FIG. 10 is a table of a partial listing of 10-bit MAPs used to determine the parameters of FIG. 9, in accordance with an embodiment.

FIG. 11 is a table of a partial listing of frequency allocations to various channels to 30 illustrate FAT shifting, in accordance with an embodiment.

DETAILED DESCRIPTION

Figure 1:
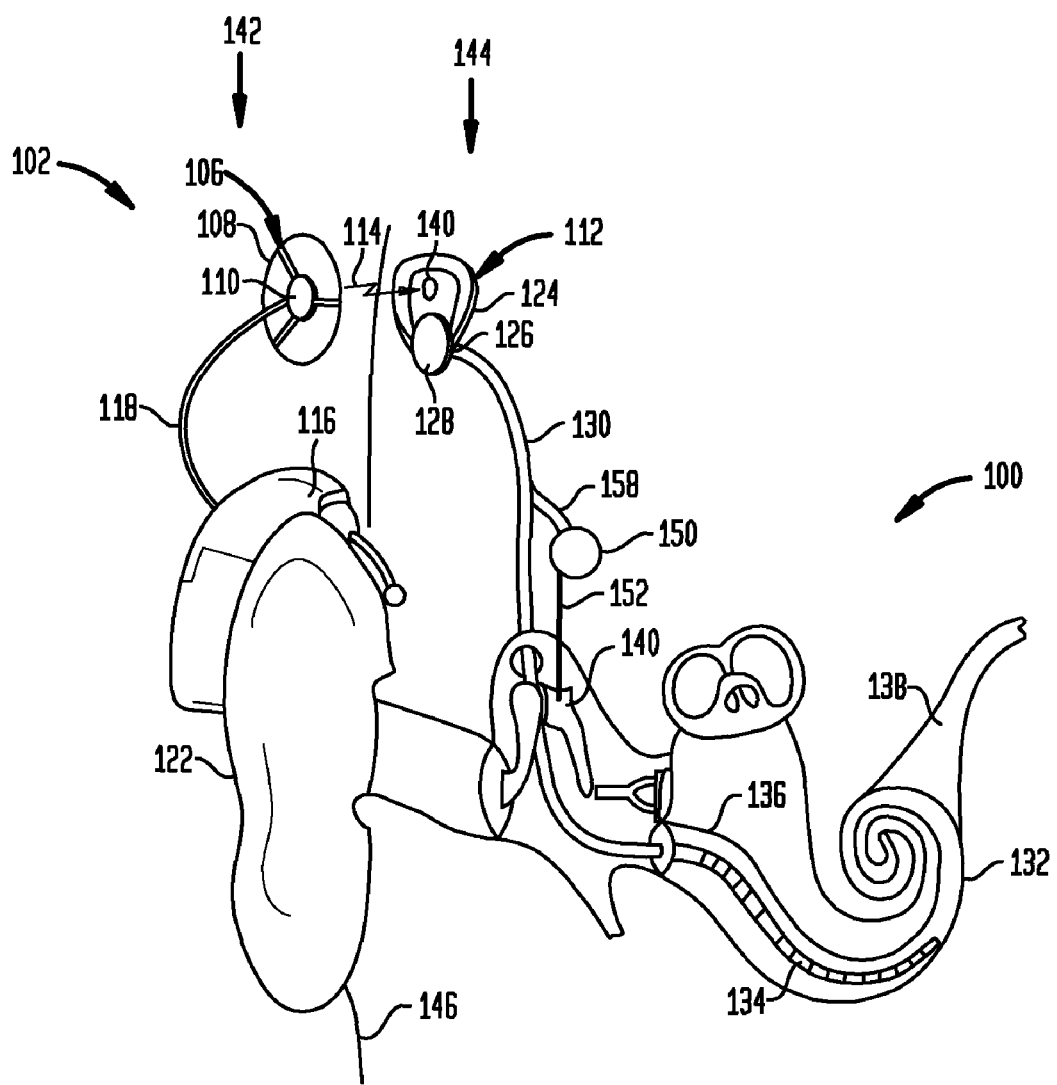
FIG. 1 is a simplified perspective view of internal and external components of an exemplary cochlear implant system shown in their operational position on a patient, in accordance with an embodiment.

Section Outline
  A. Introduction
  B. Exemplary Environment
  C. Exemplary Genetic Algorithm Search—bit string MAP representations
  D. Exemplary Enhancements
    1. Tabu Search
    2. Overloaded Generations
    3. Tagging
    4. Amplification
  E. Exemplary Fitting System Arrangement
  F. Exemplary Genetic Algorithm Search—parameter based MAPs
    1. Variable Selection—Exemplary GUI
    2. Search Diversity as a Stopping Criteria
    3. Overloaded Generations,
    4. Tagging and Amplification
    5. Tabu
  G. Alternative Exemplary GUI A. Introduction Aspects of the present invention are generally directed to using a genetic algorithm to find a solution that best fulfills specific criteria. A genetic algorithm is a procedure based on a model of biological evolution and implements aspects of evolution including, for example, natural selection and procreation with inheritance. The underlying premise is that the evolutionary process will, over multiple generations, produce an optimal organism. Accordingly, a genetic algorithm procedure may be employed to search for an optimal solution from amongst a population of possible solutions. Such a search is referred to herein as a genetic algorithm search.

It is generally desirable that a genetic algorithm search have a high amount of diversity. Diversity refers to the variability in the possible solutions considered during the genetic algorithm search. As an example, if a particular parameter has four (4) possible values, then a genetic algorithm search that considers solutions (also referred to herein as visiting a solution) including each of these four values is considered more diverse than a search where solutions are visited that only include one of the possible values.

Genetic algorithms have traditionally been used in areas in which the solution is fixed; (i.e., does not vary over time) and may be objectively determined. As such, subtle differences between possible solutions can be detected and measured. In contrast, in other technological arenas, the solution may not be fixed or objectively determined. For example, the optimal configuration of a medical device may be different for each patient, and the optimal configuration for a particular patient may be based on the patient's personal preferences. Additionally, what is considered the optimal solution may vary based on a variety of uncontrollable factors, such as how tired the patient may be, etc. Also, the optimal configuration may change over time. For example, a recipient's judgment of what is considered good or bad may change with time. Thus, what a recipient may consider to be good in an early generation of the genetic algorithm search may no longer be considered as good in later stages due to, for example, adaptation of the recipient's ear to the test or changing preferences of the recipient. Or, for example, if the genetic algorithm search takes a significant amount of time, the patient may lose interest and their responses become degraded. As such, it is desirable that, in fitting, the genetic algorithm quickly converges on a solution to minimize the impact of these factors.

Another factor impacting the performance of genetic algorithms in fitting a medical device is that a patient is often unlikely to be able to finely distinguish between slight deviations in possible solutions. For example, if the patient is presented with a plurality of choices that are all bad, the human patient is likely to judge all as equally bad rather finely distinguish between solutions that are slightly better or slightly worse than others. Similarly, when the patient is provided with choices that are close to optimum, such as when the genetic algorithm is close to completion, the patient is likely to simply identify all choices as equally good. Traditional genetic algorithms, however, depend on accurate judgments on the differences among such bad and good options in order to evolve towards better solutions.

The embodiments described below present techniques that may be used to help account for the above discussed factors. Further, certain of these techniques may be traded off against one another to help balance the competing goals of both ensuring that the search is highly diverse and that the genetic algorithm search is completed quickly.

These techniques may include: overloaded generations, amplification, tagging, tabu, diversity of the search as a stopping criteria, and variable selection. Overloaded generation, refers to using reproduction techniques wherein the number of generated children exceeds the number of solutions presented to the patient in each iteration of the genetic algorithm. Exemplary reproduction techniques that may be used for generating overloaded generations include using multiple cut points and/or multiple parent pairings in generating child solutions, each of which is discussed in more detail below. Amplification refers to a technique that leverages this increased likelihood of duplicate solutions in an overloaded generation by replacing all but one of the duplicates with a new solution, such as, for example, a solution comprising a parameter value(s) that has not yet been visited or has been less frequently visited.

Tagging refers to a technique in which good solutions are identified and tagged. Then, this tag may be used in reproduction to increase the likelihood that child solutions generated from these tagged solutions are represented in a subsequent generation presented to the patient. Tabu refers to a technique in which bad solutions are identified and pruned from the population of possible solutions such that bad solutions are not represented in subsequent generations of the search.

Using diversity of the search as a stopping criterion refers to a technique that uses a diversity measure of the genetic algorithm search (as opposed to the diversity of the solutions) in determining when to stop the search. Variable selection refers to a technique in which the number of solutions selected by the patient in each iteration of the search may vary. This technique may help to minimize the inability of patients to finely distinguish between solutions of similar quality.

Further, traditional genetic algorithms represent possible solutions using bit strings as indices into the search space. Although the above-noted techniques may be used in systems in which the solutions are represented by bit strings, an embodiment will be discussed below in which parameter based solutions are used. As discussed further below, in these parameter based solutions, the parameter values are directly included in the solutions used during the search as opposed to using bit strings that represent values in a lookup table. Further, the bit strings used in traditional genetic algorithms allow for the values represented by the bit strings to be adjusted on a continuum. In contrast, in fitting a medical device, the possible parameter values may have discrete settings (i.e., a finite alphabet of possible values). Additionally, certain values for certain parameters of a medical device may be incompatible with certain other parameters values. As will be discussed in more detail below, in embodiments, the genetic algorithm search may include a check regarding the validity of a possible solution before including it within the search.

Although the below discussed embodiments present a genetic algorithm employing each of the above-noted techniques to provide a genetic algorithm that is both highly diverse and quickly converging, it should be noted that in other embodiments these techniques may be used individually. Further, although the below discussed embodiments are discussed with reference to fitting a medical device, these techniques may also be applicable to fitting other types of devices or non-fitting applications. For example, these techniques may be used in searching for solutions for problems in which the environment changes, such as due to human impact. Or, for example, these techniques, such as, overloaded generations, amplification, and tagging, could also be used in a genetic algorithm in more traditional areas for genetic algorithms, such as engineering design.

B. Exemplary Environment

Embodiments of the present invention are described below in connection with one embodiment of a medical implant such as a cochlear prosthesis (also referred to as a cochlear implant system, cochlear prosthetic device and the like; generally referred to herein as a "cochlear implant system"). As used herein, the term "cochlear implant system" refers to partially- or completely-implantable devices that provide electrical stimulation as well as devices that provide both, electrical and mechanical stimulation to a patient to improve and/or provide hearing sensations.

Electrical stimulation may be provided, for example, to a patient's cochlea, or other parts of a patient's auditory pathway. Mechanical stimulation may be provided acoustically, that is, via airborne pathways, or physically such as with a mechanical transducer, or other electromechanical device now or later developed, to any point in the auditory pathway. Accordingly, cochlear implant systems, which may be at least partially fitted using a genetic algorithm, in accordance with an embodiment, may provide single-mode (electrical) stimulation or mixed-mode (electrical and mechanical) stimulation. Mixed-mode stimulation encompasses, for example, providing electrical and mechanical stimulation to the same ear (sometimes referred to as "hybrid stimulation"); electrical stimulation to one ear and mechanical stimulation to the other ear (sometimes referred to as "bimodal stimulation"); and hybrid stimulation to one ear and either mechanical and/or electrical stimulation in the other ear (sometimes referred to as "combined stimulation"). Additionally, in embodiments, a binaural cochlear implant system may be used in which stimulation (electrical, mechanical, or a combination of same) is provided to both of the recipient's ears. For example, in an embodiment a cochlear implant may be fitted to each of the recipient's ears, or a cochlear implant fitted to one of the recipient's ears and a hearing aid or bone conduction device fitted to the patient's other ear, or a bone conduction device fitted to each of the recipient's ears, etc.

FIG. 1 is a schematic diagram of an exemplary cochlear implant system 100 which may be fitted to an individual patient in accordance with embodiments of the present invention. This embodiment of cochlear implant system 100 has single- and mixed-mode operational capabilities. With regard to an electrical stimulation mode of operation, cochlear implant system 100 provides direct electrical stimulation of auditory nerve cells to bypass absent or defective hair cells that normally transduce acoustic vibrations into neural activity. In this illustrative embodiment, cochlear implant system 100 comprises external component assembly 142 which is directly or indirectly attached to the body of the patient, and an internal component assembly 144 which is temporarily or permanently implanted in a patient. External assembly 142 typically comprises at least one audio pickup device such as a microphone (not shown) for detecting sounds, a speech processing unit 116 that converts the detected sounds into a coded signal, a power source (not shown), and an external transmitter unit 106. External transmitter unit 106 comprises an external coil 108, and, preferably, a magnet 110 secured directly or indirectly to external coil 108. Speech processor 116 processes the output of the audio pickup devices that may be positioned, for example, by the ear 122 of the recipient. Speech processor 116 generates stimulation signals which are provided to external transmitter unit 106 via cable 118.

Internal components 144 comprise an internal receiver unit 112, a stimulator unit 126, and an electrode array 134. Internal receiver unit 112 comprises an internal receiver coil 124 and a magnet 140 fixed relative to internal coil 124. Internal receiver unit 112 and stimulator unit 126 are hermetically sealed within a housing 128. Internal coil 124 receives power and data from transmitter coil 108. A cable 130 extends from stimulator unit 126 to cochlea 132 and terminates in an electrode array 134. The received signals are applied by array 134 to basilar membrane 136 thereby stimulating auditory nerve 138. Typically, the electrodes differentially activate auditory neurons that normally encode differential pitches of sound.

Collectively, transmitter antenna coil 108 (or more generally, external coil 108) and receiver antenna coil 124 (or, more generally internal coil 124) form an inductively-coupled coil system of a transcutaneous transfer apparatus 102. Transmitter antenna coil 108 transmits electrical signals to the implantable receiver coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone molding (not shown). In use, implantable receiver unit 112 may be positioned, for example, in a recess of the temporal bone adjacent ear 122 of the recipient.

Regarding the mechanical mode of operation, cochlear implant system 100 provides, in this illustrative embodiment, direct mechanical stimulation to the patient's middle ear.

Electromechanical transducer 150 is coupled to the middle ear or inner ear using any technique now or later developed. Transducer 150 stimulates the impaired inner ear by direct mechanical coupling via coupling element 152 to a middle ear ossicle or via an air gap coupling for implantable transducers which are electromagnetic, for example. In this illustrative embodiment, electromechanical transducer 150 is coupled to incus 140. One example of transducer 150 is described in U.S. Pat. No. 5,277,694 which is hereby incorporated by reference herein. In the embodiment of a hermetically tight transducer described therein, a housing wall of the transducer is designed as a vibrating membrane which, together with a piezoelectric ceramic wafer applied to the inside thereof, comprises an electromechanically active composite element, the mechanical vibrations of which are transmitted to the ossicular chain via a coupling rod 152 permanently attached to the outside of the membrane. Optionally, coupling rod 152 can be attached to the membrane via a coupling element which is connected to the coupling rod. Alternatively, transducer 150 can be implemented as described in U.S. Pat. No. 6,123,660 which is hereby incorporated by reference. In such an embodiment, a permanent magnet is attached to the inside of the piezoelectric ceramic wafer to interact with an electromagnetic coil, such as an electromagnetic transducer. Such a combined piezoelectric-electromagnetic transducer is advantageous in particular with respect to a wide frequency band and achieving relatively high vibration amplitudes with comparatively small supplied energy.

In an alternative embodiment, transducer 150 can be an electromagnetic transducer arrangement as is described in commonly owned U.S. Pat. No. 6,162,169 which is hereby incorporated by reference herein. In such an embodiment, the transducer arrangement comprises a housing which can be fixed at the implantation site with reference to the skull, with a mechanically stiff coupling element which can move relative to the housing. In the housing there is an electromechanical transducer which to vibrates the coupling element.

The above signal processing components are controlled by a microcontroller included, for example, in speech processor 116. The microcontroller includes a storage area in which patient-specific audiologic adaptation parameters and the audiometry parameters of the above-noted signal generator are stored. The microcontroller and associated data storage may be implantable, such as within stimulator unit 126. In such embodiments, the programmable data are sent to the microcontroller via telemetry unit 102.

As noted, there may be a substantial number of parameters which may be customized to optimally fit a cochlear implant system to an individual patient. As will be described below, not all parameters may be selected to obtain values with the genetic algorithm. The selected subset of parameters and their respective values are collectively and generally referred to herein as a "parameter map," a "cochlear map" or "MAP." A "MAP" is also sometimes referred to as a "program." Because of the number of parameters which may be selected, and because such parameters may interact non-linearly and non-monotonically, selection of the parameter combination which will provide the best possible outcome for an individual patient or best sound quality to an individual patient has been heretofore difficult to obtain.

Examples of parameters include, for example, the speech strategy implemented in the cochlear implant system. Additionally, within any given speech strategy a great many parameters and parameter values may be specified to tailor the encoding and stimulation for an individual patient. Examples of parameters that may be selected for a speech strategy include but are not limited to the number of channels of stimulation represented, the configuration and number of intracochlear and/or extracochlear electrodes which are to be associated with each channel, the pulse repetition rate for each channel, the pulse pattern, the width of each pulse or between pulses, the number of spectral maxima periodically chosen for representation, the mapping of sound pressure to stimulus current for each channel (threshold levels, comfort levels and compression curves), the frequency boundaries allocated for each channel, parameters for the front end filtering of the audio from the microphone (pre-emphasis), an automatic gain control threshold, channel-specific compression ratios, and attack and release times.

In cochlear implant systems such as system 100 described above which provide electrical and mechanical stimulation, additional parameters may be selected to tailor the cochlear implant system to an individual patient. Such parameters include, but are not limited to, loudness parameters such as long term loudness balance (that is, electrical and mechanical gains), parameters for short term gain manipulations, particularly signal-dependent gain adjustments. Such gain adjustment parameters include, for example, parameters for adjustments to minimize cross-modal masking, and adjustments to emphasize speech features such as noise, frication or voicing.

Additional parameters may include frequency domain parameters. Such parameters include, for example, overall frequency boundaries allocated to electrical and mechanical stimulation, slopes of filtering at the boundaries of each stimulation signal, allocation of frequency subbands (both quantity and boundaries) in each domain, etc. Also, filtering of the mechanical signal within the passband, for example, to match the hearing loss or for other purposes.

Additional parameters may also include time domain parameters. Such parameters include, for example, parameters for adjusting electrical periodicity of pulse timing to be synchronized with the mechanical signal fluctuations, adjusting delays in the electrical stimulus to compensate for missing propagation delays of various middle ear and inner ear pathways, etc.

Additional parameters may also include binaural parameters. Such parameters include, for example, parameters for adjusting stimulus timing to preserve interaural timing cures, adjustment of stimulus timing to suppress echo, improve localization, or improve sound source segregation, etc.

As used herein, the term 'parameter values' generally and collectively refers to values of parameters, whether selectable options are programmed on or off, and in general to any choices that are made during a fitting procedure. As one skilled in the art would appreciate, the above parameters are examples of parameters which may be selected and tailored to optimally fit a single-mode (electrical stimulation) and for mixed-mode (electrical and mechanical stimulation) cochlear implant system to a patient.

C. Exemplary Embodiment

Bit String Representations

As noted, an embodiment is directed to utilizing a genetic algorithm to fit a cochlear implant to a patient. A genetic algorithm is an adaptive procedure, based on a model of biological evolution, which can be used to find optimal solutions to a problem. The procedure implements aspects of evolution, including "natural selection," "procreation with inheritance," and "random mutation." The underlying premise is that the evolutionary process will, over multiple generations, produce an optimal "organism;" that is, an organism that is best suited for its environment.

Each iteration of a genetic algorithm procedure begins with one generation of organisms and produces a succeeding generation. This typically involves two steps, selection and procreation. Selection involves the choosing of a subset of organisms as potential "parents" of the organisms of the succeeding generation ("children"). Procreation involves the creation of children from the selected sets of potential parents (usually pairs).

In genetic algorithms, selection operates on strings of binary digits stored in the computer's memory, and over time, the functionality of these strings evolves in much the same way that the DNA of species naturally evolve. Genetic algorithms are capable of evolving surprisingly complex and interesting structures. For example, such structures may represent not only solutions to problems, but also strategies for playing games, visual images, or even simple computer programs. The Darwinian theory of evolution depicts biological systems as the product of the ongoing process of natural selection. Likewise, genetic algorithms allow the utilization of computers to evolve solutions over time, instead of designing them by hand. Because almost any method, theory or technique can be programmed on a computer, this implies an approach to problem solving that can be, at least partially, automated by a computer.

The basic idea of a genetic algorithm is that first a population of organisms is created in a computer (typically with genes stored as binary strings in the computer's memory), and then the population is evolved with use of the principles of variation, selection, and inheritance. There are many ways of implementing a genetic algorithm, but the most basic is that suggested by J. H. Holland, in Adaptation in Natural and Artificial Systems, Univ. of Michigan Press, Ann Arbor, Mich., 1975, reprinted by MIT Press, Cambridge, Mass., 1992, which is hereby incorporated by reference herein.

Each of a group of organisms in a "generation" is assigned a fitness value by a fitness function. On the basis of these fitness values, the selection function evaluates the organisms. After selection, genetic operators are applied probabilistically; some organisms may have bits in their genes mutated from a 1 to a 0 or a 0 to a 1, and parts of different organisms' genes are then combined into new ones. The resulting population comprises the next generation and the process repeats itself.

The fitness function is the primary place in which a traditional genetic algorithm is tailored to a specific problem. Once all organisms in the population of a particular generation have been evaluated, their fitness values are used as the basis for selection. Selection is implemented by eliminating low-fitness individuals from the population, and inheritance is often implemented by passing on characteristics of high-fitness individuals to subsequent ones. Genetic operators such as mutation (flipping individual bits) and crossover or inheritance (exchanging sub-strings of two organisms to obtain two offspring) are applied probabilistically to the selected individuals to produce new organisms. By replacing members of the old generation with such new organisms, new generations are produced so that the old generation is completely replaced ("synchronously"), or so that the new and old members of the generation overlap ("asynchronously"). The genetic operators have been shown to generate new organisms that, on average, are better than the average fitness of their parent organisms. Therefore, when this cycle of evaluation, selection, and genetic operations is iterated for many generations, the overall fitness of the population generally improves, on average, and the organisms represent improved "solutions" to the specific problem.

Selection and reproduction can be performed in any of several ways. It can arbitrarily eliminate the least fit organisms of the population and make one copy of all the remaining organisms, it can replicate organisms in direct proportion to their fitness, or it can scale the fitnesses in any of several ways and replicate organisms in direct proportion to their scaled values (a more typical method). Likewise, the crossover operator can pass on both offspring to the new generation, or it can arbitrarily choose one to be passed on. These and other variations of the basic algorithm are well known in the art.

As noted, an embodiment is directed to using a genetic algorithm to optimally fit a cochlear implant to a patient. Specifically, embodiments may be directed to executing a genetic algorithm to select values for a subset of all the parameters for which values are to be selected to at least partially fit the cochlear implant system. In one embodiment, the genetic algorithm operates to generate successive generations of multiple groups of values for this parameter subset. Patient feedback during execution of such a genetic algorithm determines the multiple groups of subset values in each of the successive generations. Selection is thus based on the perceptual auditory judgment of the patient during execution of the genetic algorithm. In each generation, less than all (for example, half) of the groups of values for the parameter subset are selected and used to determine a larger number of groups of values for the next generation (e.g., twice as large, if it is desired that all generations be of the same size). Values for the parameters outside the subset are selected by any method now or later developed that does not use a genetic algorithm. Typically, most of the parameters are not selected by using a genetic algorithm. For example, in one illustrative embodiment, the subset of parameters selected by a genetic algorithm for the electrical stimulation mode of operation include parameters relating to those characteristics commonly considered by clinicians to be important in the fitting process: rate, number of channels and filtering characteristics.

In an embodiment, an 'organism' is defined by a set of $N_b$ 'genes' (bits), with the number of possible unique organisms is $2^{Nb}$. In connection with an embodiment, the organism to be optimized is a cochlear map. As noted, such a MAP is a collection of parameters and their values. Although the present embodiments are discussed with reference to MAPs represented by bit strings, it should be understood that in other embodiments the MAPs may be represented by other data structures, such a data structures storing the actual parameter values (referred to herein as parameter based MAPs) as opposed to a bit string representation of the parameters and their values. An exemplary genetic algorithm search employing parameter based MAPs is discussed in more detail below, such as, for example, with reference to FIG. 13.

Figure 2A:
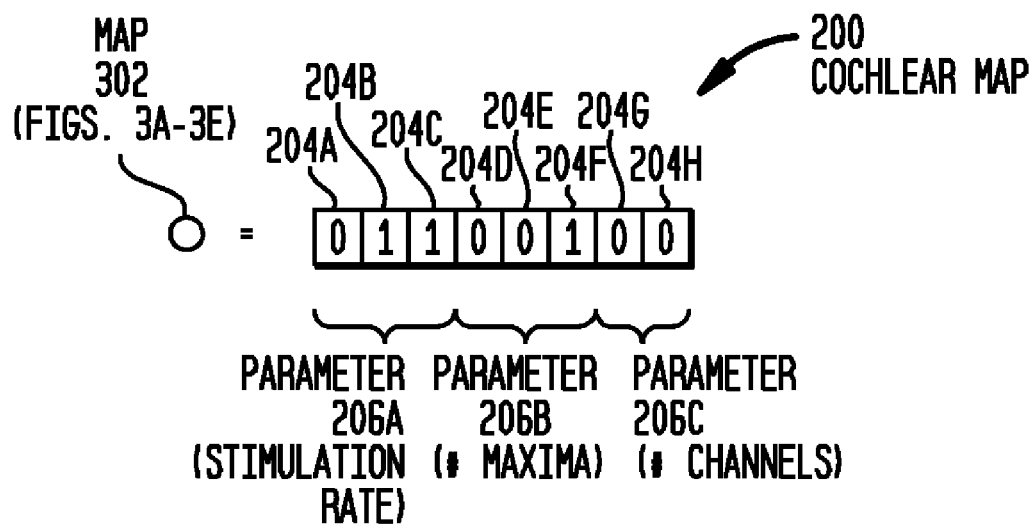
FIG. 2A depicts how specific bits in a bit string can represent values of respective parameters, in accordance with an embodiment.

In the exemplary cochlear map 200 illustrated in FIG. 2A, there is a set of 8 binary genes 204A-204H ($N_b$=8) so MAP 200 is defined by a gene set or string of 8 bits 204 forming 256 possible MAPs 200. MAP 200 is an example of the organisms 302 shown in FIGS. 3A-3E described below. Each of the 8 bits 204 may be used to individually or collectively designate several parameters for cochlear implant system 100. In the example shown in FIG. 2A, three such parameters 206A-206C are designated. Three bits 204A-204C are used to select a parameter 206A of stimulus rate (the rate, in Hz, at which high-energy channels are selected and stimulus pulses are delivered to groups of N electrodes), three bits 204D-204F are used to select a parameter 206B of spectral maxima counts (the number N of electrodes periodically selected to be stimulated, representing the N frequency bands with the highest energy at the time), and the remaining two bits 204G-204H select a parameter 206C of the quantity of channels or frequency bands, used to represent the sound spectrum. Other parameters are assumed to be constant or derived from one of the three represented parameters 206; they are fitted using traditional methods. As discussed in more detail below, the number of bits for each cochlear map 200 and the number of parameters 206 defined by the MAPs may be different in alternative embodiments.

In a genetic algorithm, a 'generation' can be considered to be a set of one or more organisms. Generally, the number of organisms Ng is constant from generation to generation although that need not be the case. In one embodiment, the initial generation comprises a selection of 8 different MAPs as illustrated in FIG. 2A, which span the parametric ranges. These MAPs may be completely random. Alternatively, some or all MAPs of the initial generation may be the preferences of the patient or clinicians, or may be selected from the results of a previous execution of the method, as discussed in greater detail below.

A 'fitness function' is used to evaluate each of the organisms in each generation. The fitness function identifies which organisms will survive to become parents and procreate, and which of the organisms die. Generally, the number of survivors is constant from generation to generation, although that need not be the case. In one embodiment, a fitness function is used that causes half of the organisms survive.

In an embodiment, the fitness function is a listening test performed by the patient. For example, the patient may listen to speech presented through each of the MAPs in a generation, and selects, for example, half of the MAPs that produce the best intelligibility. Note that the patient need not rank groups of subset values from best to worst. With eight groups per generation, for example, the patient simply has to choose the four he or she likes best. Or, for example, as will be discussed in more detail below, in an embodiment, the patient may simply identify which MAPs produce good intelligibility and these MAPs producing good intelligibility are then used as parents to spawn subsequent generations.

Alternatively, the fitness of a MAP may be determined entirely, or in part, from objective measures, that is, measurements not involving a judgment by the patient, such as cortical or brainstem evoked potentials measured from the patient, the patient's ability to repeat a speech token, the quality of a the patient's speech while listening to his/her own speech with a selected cochlear map, results of an objective speech reception test, or expert knowledge about known beneficial parameter combinations.

Figure 3A:
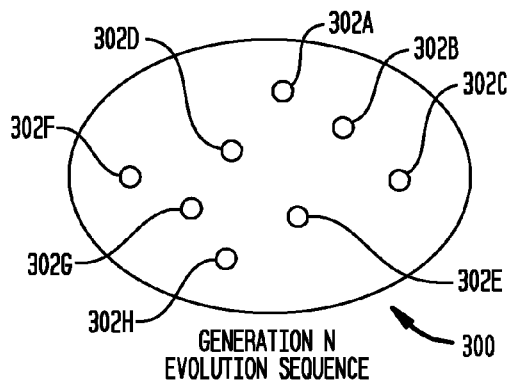
FIGS. 3A-3E depict successive states in the performance of the genetic algorithm for a specific generation in accordance with an embodiment.
Figure 3B:
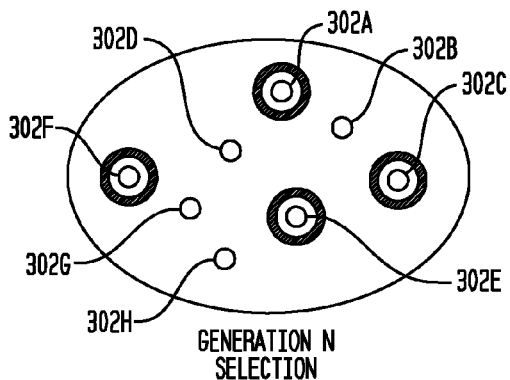
Figure 3C:
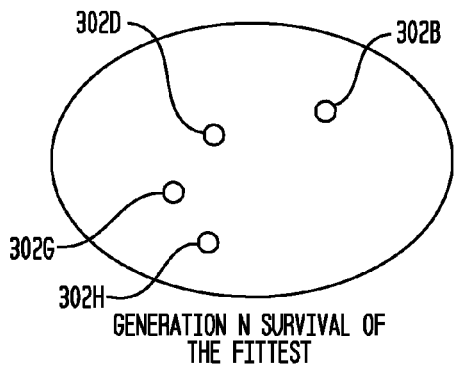
Figure 3D:
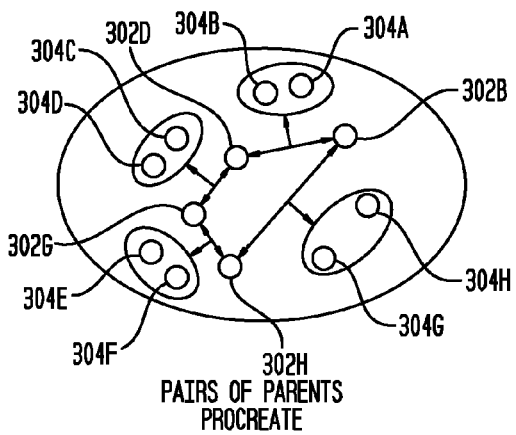
Figure 3E:
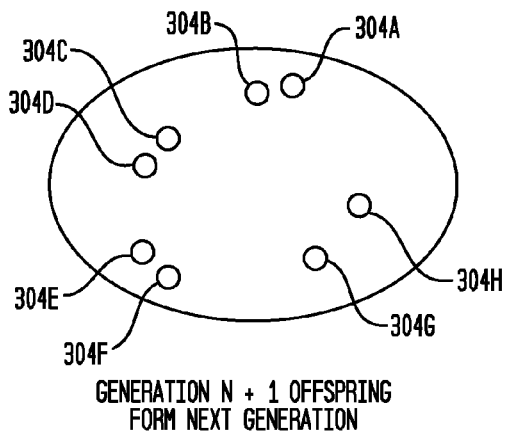

'Reproduction' involves three separate operations: pairing of parents, inheritance, and mutation. For example, FIG. 3A depicts an arbitrary generation N in an overall sequence 200 that has evolved to contain 8 organisms or individuals 302A-302H. The 'fitness function' rejects four of these organisms: 302A, 302C, 302E and 302F (these organisms are circled in generation selection 304 illustrated in FIG. 3B). FIG. 3C showing the survivor organisms 302B, 302D, 302G and 302H in the survival of the fittest illustration 206. The survivors are then paired, as shown in FIG. 3D, with each survivor 302B, 302D, 302G and 302H mating with two other survivors. Each pair produces two children 304A-304H. The 8 children 304 make up generation N+1, as shown in FIG. 3E.

In one illustrative embodiment, a round-robin algorithm is used to identify pairs of parents 302 in each generation, with each pair producing several children 304. In one particular embodiment, each pair of parents 302 produces two children 304. For example, 8 MAPs can be arranged into four pairs of parents 302 resulting in a new generation of 8 children 304. Each child 304 inherits some of its 'genes' from each parent 302. For example, the string of bits of each MAP can be partitioned by boundaries into sub-strings that constitute "genes." Finally, after reproduction, each gene is, optionally, subject to random inversion (mutation). Preferably the probability of each mutation is small. Typically this probability may range from 1 to 10%. In one embodiment, the mutation probability is approximately 3%.

In one embodiment, the genetic algorithm includes performing reproduction on an initial generation several times, and then using the last or final generation to program a cochlear implant system such as system 100. Embodiments of this process are described next below. FIG. 2A is an illustration of an organism 200 represented by the leftmost circle 302 in FIG. 2A and corresponding to the circles in FIGS. 3A-3E. In this example, organism 302 is a MAP 200 defined by a set of 8 binary bits or genes 204A-204H. In this case, the 8 bits 204 have been partitioned into three sub-strings 206A-206C, each corresponding to a parameter. The first set 206A of 3 bits 204A-204C represents 1 of 8 stimulation rates, the second set 206B of 3 bits 204D-204F represents 1 of 8 maxima counts, and third set 206C of 2 bits 204G-204H represents 1 of 4 channel counts. For each of the 8 stimulation rates, a corresponding set of threshold (T) and comfort (C) levels, one for each electrode, is also selected. Ts and Cs may be determined, for example, by clinician measurement at the corresponding rate, or by inference, using a mathematical loudness model, from Ts and Cs measured at a single standard rate. For each MAP 200, appropriate T and C levels are used for each stimulation rate.

Figure 4:
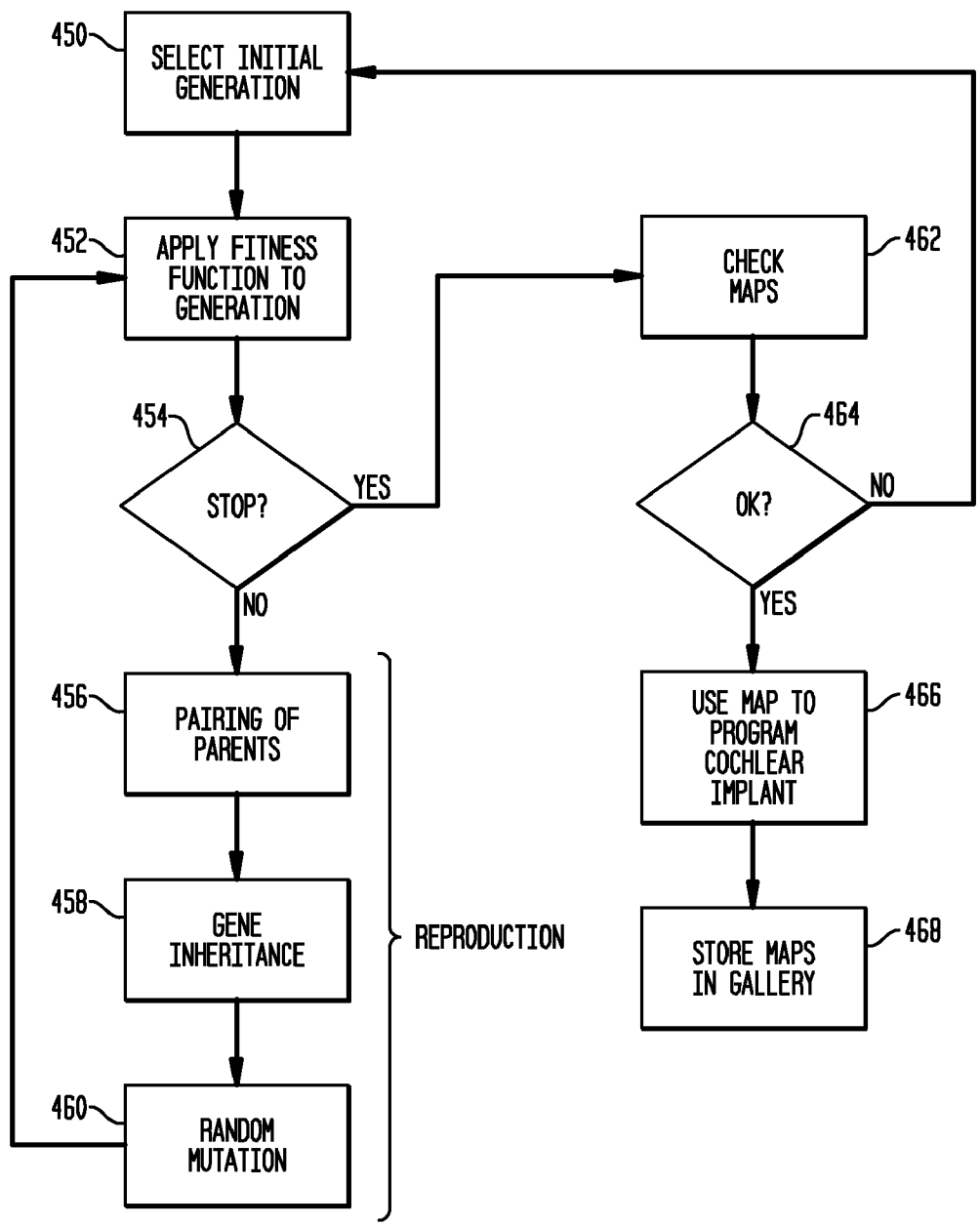
FIG. 4 is a flow chart of the operations performed to determine a parameter map using a genetic algorithm, in accordance with an embodiment.

FIG. 4 is a flow chart of the operations performed to determine a MAP using a genetic algorithm, in accordance with an embodiment. This presently described flow chart will be discussed with regard to bit string MAP representations, however, it should be understood that in embodiments parameter based MAPs may be used. Further, although FIG. 4 does not illustrate some of the above noted enhancements, such as overloaded generations, it should be understood that this was done for simplification, and embodiments employing each (or a subset of) these enhancements may be used. Further, a more detail description of parameter based MAPs, and enhancements, such as overloaded generations and tabu is discussed in more detail below, such as with reference to the flow chart of FIG. 13.

Referring to FIG. 4, initially at block 450, a generation of eight MAPs 200 is selected. Initialization involves the selection of a first generation of designs. This selection may be performed by selecting at random from among the set population of possible MAPs. Preferably, in order to insure that this initial MAP set has a sufficient measure of heterogeneity, its diversity is computed. In one embodiment, diversity is defined as the average Hamming distance between the various MAPs, and it ranges between 0 and 1, with 1 indicating maximum diversity and 0 indicating minimum diversity. If the diversity is below a threshold, for example, 0.53, then the initial generation has is determined to have an insufficient diversity, and a new set of MAPs is selected. Moreover, preselected MAPs may also be included among the MAPs of the first generation. These pre-selected MAPs may be drawn from prior runs of the fitting procedure, MAPs from a patient specific database of MAPs (referred to as the implant patient's gallery) or MAPs selected by a clinician based on his experience, suggestions and recommendations from others, etc. The pre-selected MAPs may, for example, be stored in a storage internal or external to a fitting system, such as discussed in more detail below.

Next, at block 452 the fitness function is applied to the initial generation. That is, the parameters corresponding to the eight MAPs 200 are sequentially programmed into a cochlear system or emulator and tests are performed to determine which subset of the generation provides better results. As described above, these tests may be tests based on the perception of the patient, objective tests during which some physiological measurements are taken, or a combination of both types of tests.

For example, as part of the fitness function, the patient may be asked to listen to a sound token (e.g., a speech token) for each of the eight MAPs. The patient may listen to each token as many times as the patient prefers. In one embodiment, the tokens are selected from a library of relatively long audio files (e.g., 2 minutes). Each file in such a library may include, for example, a single speaker reading aloud from a newspaper or a passage from an audio book. In one embodiment, the patient listens to the whole file. In another embodiment, the file is partitioned into shorter segments of random lengths. Each segment is then used as a speech token.

Alternatively, a library of tokens is provided, each token corresponding to a relatively short audio file. A large number of different types of audio files may be provided. The diversity between the files is used to explore how different MAPs process the files under common conditions. Each file is played in its entirety and can have predetermined lengths (e.g., four seconds). The library may include separate male and female sentence audio files. For example, the library could include 192 sentences from 64 different speakers (3 files per speaker) the speakers being male or female and having various accents or dialects. Preferably, each audio file incorporates a rich range of phonemic and contextual cuing. In an alternative embodiment, long or short audio files within a noise environment is also used as tokens in addition to or in place of the tokens described above.

Figure 5:
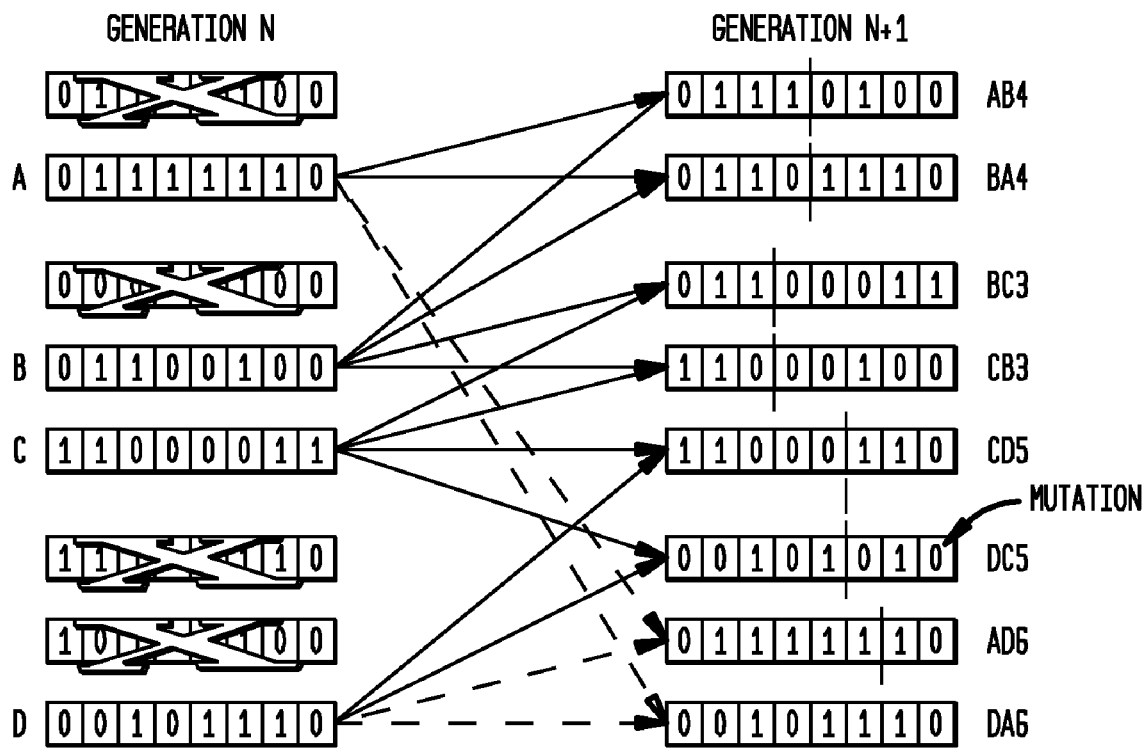
FIG. 5 is a logical block diagram showing how organisms of a generation survive and reproduce to give rise to organisms in a successive generation.

Referring now to FIG. 5, the right side of the figure shows the 8 MAPs of a generation N. At block 452, the patient determines which 4 of the 8 MAPs are the clearest, in the sense that they are more preferred by the patient. In this manner, four of the MAPs are eliminated as indicated in FIG. 5 by the large X. The remaining MAPs are designated as MAPs A, B, C and D. These MAPs are used for reproduction as described herein.

Next, at block 454 a test is performed to determine if the algorithm should be stopped. In one embodiment, the algorithm is stopped after a predetermined number of generations. In another embodiment, the diversity of the surviving MAPs is compared to a threshold. If the diversity is below a limit (e.g., 0.1) then the surviving MAPs are the final MAPs that are processed as described herein. Otherwise the algorithm continues with reproduction.

As noted, reproduction comprises three steps: pairing, inheritance and mutation. Pairing occurs at block 456. As part of this operation, each surviving MAP forms pairs with some of the other surviving MAPs. In FIG. 5, each MAP is paired with two other MAPs, forming four pairs are AB, BC CD and AD, as shown in FIG. 5. Of course other pairs are possible as well.

Figure 2B:
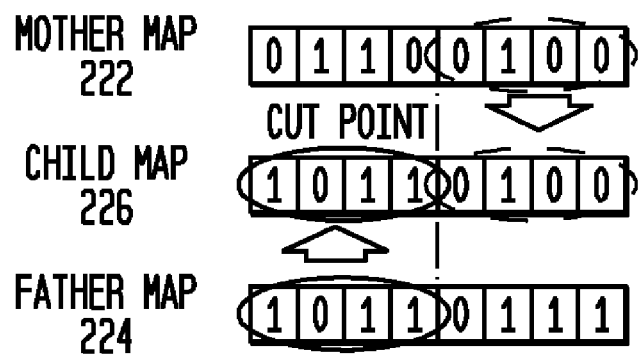
FIG. 2B illustrates how two 'parent' bit strings reproduce, in accordance with an embodiment.

The pairs of MAPs are used to generate two children or offspring at block 458. FIG. 2B shows how an offspring inherits some genes from each parent. For this purpose, a boundary or cutpoint is made in the bit string of each MAP. In FIG. 5, this boundary is established at the middle of the bit string although it may be placed at other locations in alternative embodiments. In FIG. 2B, a child MAP 226 includes the first 4 bits of the Mother MAP 222 and the last 4 bits of the Father MAP 224.

Thus, at block 458, generation N+1 results from the pairings at block 456, using predetermined criteria. This process is further illustrated on the right side of FIG. 5. The cut points govern inheritance of genes from each parent and are illustrated by the vertical dotted lines through each child on the right. Genes to the left of the cut point come from one parent, and genes to the right come from the other parent. In the illustrative example, the cut point is allowed to vary randomly across pairings. Further, in an embodiment, the fitting system may analyze the two parent MAPs to identify bits that are different between the parents, and then randomly select a cut point between the bits identified to be different. Alternatively, the cut points can be made in the same position for all the pairings.

As discussed above, in one embodiment, two children result from each pairing. The genes of each child may be selected from the genes of the parents in different ways. In one embodiment, the genes of one child include the genes from the left side of the cut in one parent and the genes from the right side of the cut from the other parent (as illustrated in FIGS. 3B and 3C). The genes for the other child are selected by copying the genes on the right side from the first parent and the left side from the second parent. Bits common to both parents are repeated.

More specifically, in FIG. 5, each child is identified by a notation such as CDS. The first letter represents the organism in generation N that contributes leftmost bits to the child in generation N+1, the second letter represents the organism that contributes rightmost bits, and the numeral represents the position of the cuts. Lastly, as part of reproduction, a mutation is performed at block 460. Mutation is implemented by inverting some of the bits of at least some of the children in an arbitrary and random manner. For example, in FIG. 5, the last or least significant bit in the sixth child of the new generation N+1 is inverted.

Once the new generation N+1 is formed, the fitness function is applied again at block 452 and the process continues.

The four final MAPs found at block 454 are checked further at block 462 to insure that their parameters are acceptable. In other words, a check can be performed to determine if the MAPs are valid, permissible, admissible or even realistic. If these final MAPs are not acceptable at block 462 then they are returned to the genetic algorithm. Alternatively, a different initial generation is selected at block 450 and the genetic algorithm is repeated. Alternatively, the operations at block 462 can be omitted.

If the final MAPs are found acceptable at block 464 then one of them is selected and used to program the cochlear implant system 100 at block 466 and stored at block 468. Alternatively, all the MAPs may be presented to the patient and the patient may be allowed to select the MAP that seems to perform best.

The 8 bits that represent a unique MAP, in the presently discussed embodiment, give rise to 256 possible different bit strings that represent 256 unique MAPs. Several methods may be used to correlate each MAP to a corresponding set of parameters. Three such methods are discussed below.

FIG. 6 is a logical block diagram illustrating a manner in which a MAP formed of a bit string represents parameter values in accordance with an embodiment. In this embodiment, 256 predetermined MAPs are chosen. Each MAP may represent any arbitrary admissible combination of parameters. For example, 256 different combinations thought to be useful by expert clinicians could be selected. The only constraint is that each combination be admissible and unique, that is, no two MAPs may represent the same combination of parameters in this embodiment. A lookup table associates each of the 256 possible bit strings with one of the 256 available MAPs. Therefore, when a bit string is specified, it uniquely represents a single MAP. With this method, each parameter can have any legal value in each MAP. For example, each of the 256 possible MAPs might have a different rate. In the embodiment illustrated in FIG. 6, five parameters are varied within the set of 256 MAPs.

In one exemplary embodiment, various, but not all, combinations of the following parameters are constructed within the set of 256 possible MAPs (some of the possible combinations are not valid clinically and are rejected): (1) Stimulation rate (one of 250, 720, 1200, 1800, or 2400 Hz); (2) number of electrodes used (either 10 or 22); (3) number of maxima per stimulus frame (one of 4, 6, 8, 10, 12, 16, or 20); (4) steepness of output compression (known as the "Q" factor for an ACE or SPEAK MAP—either 20 or 30); and (5) combination of input audio filtering options (flat, high cut, low cut, or high and low cut). None of these parameters need to be individually represented by any particular subset or sub-string within the 8-bits.

Figure 7:
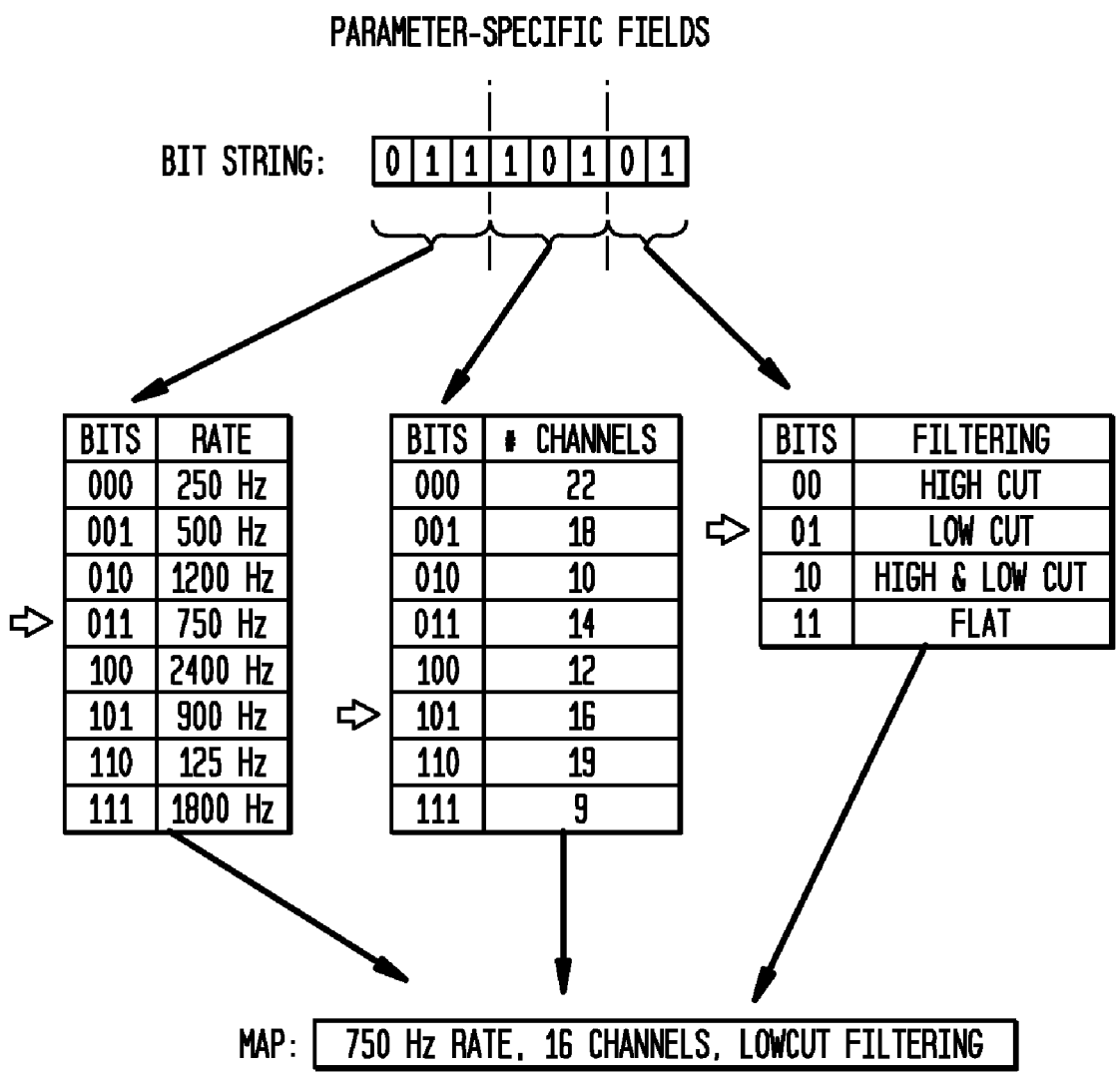
FIG. 7 is a logical block diagram illustrating a manner in which a parameter map formed of a bit string represents parameter values in accordance with an embodiment.

FIG. 7 is a logical block diagram illustrating a manner in which a MAP formed of a bit string represents parameter values in accordance with an embodiment. With this method, the bit string is broken down into sub-strings or fields. The sub-string in each field is then used to select a particular parameter for the MAP. In the example of FIG. 7, one 3-bit sub-string selects one of 8 possible rates for the MAP. A second 3-bit sub-string selects one of 8 possible channel counts, and a third 2-bit sub-string selects one of 4 possible filtering options. In this example, each sub-string is contiguous. However, this is not necessary, because there is no significance to the order of the bits in the bit string.

With this method, the available options for any given parameter are fixed by the number of bits in the corresponding sub-string. In the example of FIG. 7, only 8 different rates are available. No MAP can be defined with a rate of 792 Hz, for example, because this rate is not one of the 8 available alternatives.

Figure 8:
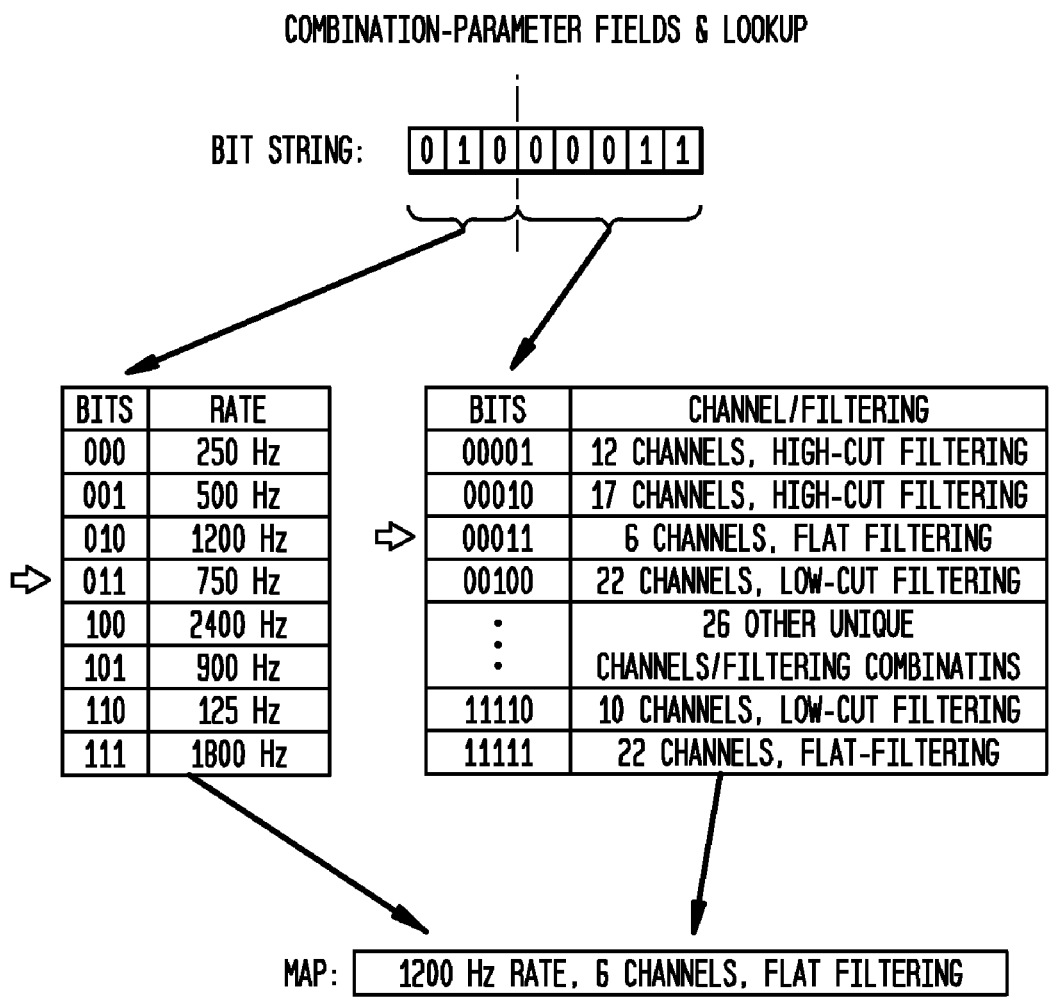
FIG. 8 is a logical block diagram illustrating a manner in which a parameter map formed of a bit string represents parameter values in accordance with an embodiment.

FIG. 8 is a logical block diagram illustrating a manner in which a MAP formed of a bit string represents parameter values in accordance with an embodiment. This method is a combination of the previous two methods. One or more sub-strings are defined to select corresponding parameters as in FIG. 7. The remaining bits are used to choose from a table of arbitrary combinations of the remaining parameters. In the example of FIG. 8, one 3-bit sub-string selects one of 8 possible rates. The remaining 5 bits are used to choose, from a lookup table, one of 32 arbitrary combinations of channel count and filtering. As with the first method, each of the 32 arbitrary combinations must be legal and unique.

FIG. 9 is a table of seven parameters that can be determined using the subject algorithm, and the possible values of each parameter, in accordance with an embodiment. As previously discussed, the number of bits per MAP is not limited to 8. If more then 8 bits are used, the process can be used to optimize more parameters. In an alternate embodiment, 10-bit MAPs are used to optimize seven parameters: the five original parameters discussed above in conjunction with the 8-bit MAPs and two new parameters, FAT shift and T-level bump. These two parameters are described in more detail below. The seven parameters and their allowable values are shown in FIG. 9.

FIG. 10 is a table of a partial listing of 10-bit MAPs used to determine the parameters of FIG. 9, in accordance with an embodiment. In FIG. 10, a listing of the first three binary MAPs used to determine the seven parameters of FIG. 9 and the respective parameter values, is shown. Some of these values are arbitrary numerical values. For example, a '1' for the FAT shift or the T-level bump designates the default value. '1', '2' and '3' for the filters designate the Low B, Low cut and high cut settings for the filters. Of course, the assignment of each set of parameter values to any 10-bit MAP is arbitrary.

It is well known in the art that a cochlear implant applies stimulation signals to the auditory nerve of a patient using a single or a plurality of electrodes. The electrodes are grouped to define channels, each channel being used to apply signals corresponding to certain audible frequency bands. Typically, a cochlear system may use up to 23 channels and during the fitting of a cochlear implant a table is designated for the system that defines the number channels to be used and the frequency band allocated to each channel.

FIG. 11 is a table of a partial listing of frequency allocations to various channels to illustrate FAT shifting, in accordance with an embodiment. Traditionally twenty seven tables are used to define up to 22 frequency bands corresponding to 22 channels. FIG. 11 is a partial listing of standardized frequency allocation tables (FATs) 6, 7, 8, 14, 15 and 16. Each table lists the upper frequency boundary of each band. The left column of FIG. 11 provides a frequency band index that identifies the rows of the listing. The rows of Table 6 indicates one possible frequency allocation for all frequency boundaries starting at 188 Hz for band 0 and ending with 7938 Hz for band 22. In fact, starting with table 6, the top frequency for the first channel is always allocated frequency 188 Hz and the top frequency for the last channel is always allocated 7938 Hz. Tables 1-5 have been omitted and contain slightly different frequency allocations to the 23 channels. Table 8 indicates the frequency allocation when 21 channels are used. Table 15 shows the frequency allocation for 14 channels. As can be seen from FIG. 11, as the number of utilized channels is reduced, the frequencies allocated to the highest channels are compressed. As a result of this compression, tables with lower number of channels provide a lower resolution of the audible signals at the high frequency ranges.

In the present embodiment, when the FAT shift parameter is set to its default value, the FAT tables of FIG. 11 are used. When the FAT shift is enabled, the tables are shifted to the left by a predetermined number of columns In the preferred embodiment, FAT tables are shifted by one or two columns. For example, if table 8 is designated with 21 channels and the FAT shift is set at the default value then the frequency allocations shown in FIG. 11 for table 8 are used. If the FAT shift parameter is at a shift value, then the frequency values of the first 21 channels of table 6 are used. Thus for no shift, the channel 20 is designated the frequency 7938 Hz. When the shift parameter is 1, the channel 20 is designated 6063 Hz. For table 16, with no FAT shift, the channel 12 is designated the 7938 Hz frequency. With shift, table 15 is designated with channel 12 being allocated to 6313 Hz. The tradeoff is that the audible signals above the frequency allocated to channel 20 (for table 8) or channel 12 (for table 16) are lost.

Two other well-known programming parameters in cochlear systems are the T and C (threshold and comfort) levels. The T-level bump pertains to a feature of an embodiment wherein the T level is raised by a predetermined ratio (for example, 10-20% of the range between the original T and C levels). This feature improves the sensitivity of the system to soft sounds.

In addition, in the preferred embodiment, the filters parameter is augmented to include low B (low frequency boost), low C level and high C level. These parameter choices reduce the C level at low and high frequency, respectively.

Because not all combinations of parameter values are possible, only 1032 MAPs are required for the parameters shown in FIGS. 9 and 10. Since 10 bits can only define 1024 MAPs, eight combinations of parameter values are arbitrarily excluded.

The details of the implementation can significantly affect the behavior and efficiency of the genetic algorithm, particularly its speed of convergence. The fitness function need not be purely subjective, e.g., it can be based on cortical evoked potentials either alone or with subjective inputs. But if the fitness function used involves subjective comparisons by a user, in implementations employing bit string representations of MAPs, it is generally desired to limit $N_g$ because a human listener cannot reasonably compare dozens of concurrent alternatives. A subjective fitness function is also 'expensive' in terms of time, which makes rapid convergence important. In general, the number of generations required for convergence rises with the number of genes per organism ($N_b$), so it is desirable to keep $N_b$ as small as possible while still representing those MAP parameters which are most likely to influence performance.

In an embodiment, at each iteration the user is given the opportunity to flag MAPs to be saved for future consideration. In this way if the process 'stumbles' onto a particularly good MAP it can be saved either at block 452 or at block 468 for comparison against the eventual result of the evolution. This eliminates the risk of frustrating the user. If multiple runs are used, saved designs, or designs resulting from a first run, can be included in the initial population for a subsequent run.

Expert knowledge can be incorporated into the process in various ways. As noted above, the MAPs of the initial generation can be based upon clinical judgment. Also specific parametric combinations known to be detrimental can be excluded from the population of possible MAPs. Conversely, specific parametric combinations known to be beneficial can be condensed into a single 'parameter;' or occurrence of a specific value of one parameter may be used to override and dictate the value of a different parameter (e.g., any time the rate is >2400 Hz, the number of channels is limited to 10). Finally, as the population evolves, the expert may serve as an auxiliary form of input to guide the evolution in particular directions. For example, the clinician, based upon a visual representation of the evolution of the parameters, may anticipate more efficient paths to an optimal region. This expert knowledge can then be used to help steer the update mechanism in the proper direction.

The method of the above-discussed embodiment has the advantage that it can be automated, requiring no supervision by the audiologist. It may also be repeated periodically as the recipient becomes more experienced. Separate optimizations may be performed for specific classes of input signals (e.g., speech in quiet, speech in noise, music, etc).

In some instances, it may be desirable to 'freeze' the values of one or more parameters after several iterations, using the value of the intermediate MAPs resulting from the iterations. For example, if at block 452 while analyzing the current generation of MAPs it is that all the survivors of a generation correspond to a subset of parameters that are identical (e.g., all the survivors have the same rate, the same number of maxima and the same number of electrodes), then these parameters are frozen. This may be accomplished in several ways. The simplest approach is to save the parameter values in a separate memory, let the algorithm run its course, and, at the end, when the final generation is obtained, substitute some of the 'final' parameters, that is, the parameters corresponding to the final MAPs with the 'frozen' parameters obtained during iterations.

Another approach is to use a different set of MAPs with lower bit series. For example, if originally 10-bit MAPs are used for eight parameters, and after some iterations, three of the parameter values are frozen, then a new set of 8-bit MAPs is used for the algorithm. The shorter MAPs used to continue the algorithm may consist of a set of initial MAPs as discussed above, or may be derived from the intermediate MAPs.

Finally, the algorithm itself may be modified so that after some of the parameters are frozen, portions of the MAPs are not changed anymore, i.e., they are not subject to gene selection. Of course, this approach is easiest to implement for MAP configurations in which all or some of bits of the MAPs correspond to, or represent specific parameter.

D. Exemplary Enhancements to Bit String Embodiment

As noted above, the above-discussed embodiments may be modified to include various other techniques. For example, although the above-discussed embodiments were discussed with reference to MAPs that were represented by bit strings, in other embodiments, data structures other than bit strings may be used in the genetic algorithm. For example, in an embodiment, the MAPs may be represented by data structures in which the actual parameter values for the MAPs are included, referred to herein as parameter based MAPs. Additionally, rather than generating a specific number of child MAPs in each generation, in other embodiments, a large number of child MAPs may be generated (referred to herein as an overloaded generation) and then various techniques may be used to reduce a number of MAPs from this large pool of child MAPs (referred to herein as culling the MAPs). These selected MAPs may then be used as the next generation of MAPs presented the patient for selection as the next set of parent MAPs. Further, rather than the patient selecting a specific number of MAPs as parents, the patient may select a variable number of MAPs as parents. Moreover, in embodiments, the genetic algorithm may be enhanced by using a tabu search. The following provides a more detailed description of these techniques.

1. Tabu Search

As noted above, embodiments may also incorporate into the genetic algorithm a tabu search algorithm. In an embodiment, a memory component of a fitting system performing the genetic algorithm search may store a tabu list of undesirable MAPs. That is, a running tabu list may be stored where "bad" MAPs are added to tabu list as they are identified. The tabu list may be used to prune the global population of the search, such that tabu MAPs are removed from the global design population and not included in subsequent phases of the search.

Referring back to the flow chart of FIG. 4, in an embodiment, a fitness function may be applied at block 452 where a patient may be asked to listen to a speech token for each of a plurality of MAPs and, in response, the patient may identify which MAPs are preferred. In such an embodiment, a MAP may be deemed "tabu" and added to the tabu list simply by the patient not selecting it as a "desirable" MAP. Because a good MAP may be identified as undesirable due to a bad speech token or noise (e.g., observer or algorithmic noise), in an embodiment, a MAP is added to the tabu list only after the patient has not selected the MAP more than once (i.e., two or more times).

As discussed above with reference to block 452, a fitting system may present eight different speech sentences/tokens processed by eight different MAPs during a single generation. The patient may then select those sentences (e.g., between 0 and 8 of the presented sentences) that are judged as "good" by some perceptual metric. The MAPs corresponding to the selected sentences may then be used as parents for the next generation. And, the MAPs corresponding to non-selected sentences may be added to the tabu list. Or, for example, to reduce the likelihood of a good MAP being added to the tabu list as the result of a bad speech token or noise, a MAP may be added to the tabu list only after the patient has not selected a sentence processed using the MAP two or more separate times.

In another embodiment, the patient may be permitted to specifically identify a particular sentence as being perceived as bad, and MAPs used to process sentences identified as bad are added to the tabu list. In order to reduce the risk of a good MAP being identified as bad, in an embodiment, a MAP may only be added to the tabu list after it has been identified as bad more than once. In such an embodiment, MAPs corresponding to unselected MAPs are not added to the tabu list simply based on not being selected, but are only added to the tabu list if they are specifically identified by the patient as bad. Or, for example, MAPs not identified as bad, but not selected by the patient, may be added to the tabu list only after they are not selected by the patient a specified number of times (e.g., three or more times).

The tabu list may persist throughout the duration of an evolution (i.e., until a final MAP is chosen for a specific patient), for a limited number of generations, or over multiple evolutions for specific subjects or in general for all subjects. Because the tabu list effectively reduces the population in later generations, it serves to focus the search on preferred or unvisited designs and population regions.

Referring back to block 458 of FIG. 4, as noted above, in an embodiment, the fitting system may generate child MAPs from parent MAPs paired at block 456. In an embodiment, this block 458 may further comprise checking whether any of the generated child MAPs are on the tabu list, and if so eliminating any such tabu MAPs from consideration. If any MAPs are eliminated, the eliminated MAPs are replaced prior to returning to block 452 in which sound tokens are presented to the patient using the child MAPs. Various techniques may be used for generating the replacement child MAPs. For example, in an embodiment, a replacement MAP may be generated by the fitting system producing an additional MAP by random mutation of one of the acceptable children at block 460. Or, for example, an additional child MAP may be generated by selecting a different pairing of parents and then randomly selecting one of the children MPA from this additional pairing of parents. Or, for example, additional children may be obtained by the fitting system selecting a different random cut point for one of the paired parents and selecting one of the resulting children with this new cut point. Additionally, in embodiments, the replacement MAPs may be obtained using tagging or overloaded generations, which are discussed in more detail below.

2. Overloaded Generations

In embodiments, reproductive methods may be used that result in overloaded generations. As discussed above, in a genetic algorithm, two parents may reproduce by identifying a single common cut point. The cut point is used to produce 2 new offspring. For instance, if parents [11111] and [00000] are chosen, reproduction using a randomly chosen cut point between the first and second bit locations will yield offspring [01111] and [10000]. However, in other embodiments, the fitting system may use alternative reproduction techniques to generate a much larger number of offspring. Then, the fitting system may cull this population of generated children to achieve the number of MAPs specified for each generation. In one such embodiment, children are generated using every possible cut point between parents, rather than just the single random cut point. Following the example above, cut points could exists between bit locations 1&2, 2&3, 3&4, and 4&5. This may result in a large pool of offspring, especially if each parent reproduced with every other parent. Further, rather than pairing each parent with a single other parent, in embodiments, every parent MAP may be paired with every other parent MAP. When every parent MAP is paired with every other parent MAP using every possible cut point, the number of generated child MAPs may be larger than the number of MAPs to be presented (i.e., MAPs that are used to process audible signals presented to the patient processed by the MAPs) to the patient in the next iteration of the genetic algorithm. Additionally, in an embodiment, the parent MAPs may also be added to the pool of children MAPs, referred to herein as bullying through the parents. When the number of MAPs in a generation of child MAPs exceeds the number of MAPs to be presented to the patient (i.e., MAPs that are used to process audible signals presented to the patient processed by the MAPs), the generation is referred to as overloaded.

If a generation becomes overloaded, in an embodiment, the number of MAPs may be reduced to a particular number (e.g., 8) for the subsequent presentation to the patient. The process of reducing the number of MAPs in an overloaded generation to a specific number of MAPs is referred to herein as culling. For example, in an embodiment, such as discussed above, 8 MAPs may be used for each generation. But, using the reproduction techniques described above may result in more than 8 children being generated for a single generation. In an embodiment, this larger number of child MAPs may be reduced to 8 MAPs and these 8 surviving MAPs may be used as the next generation of MAPs presented to the patient (i.e., MAPs that are used to process audible signals presented to the patient processed by the MAPs).

Various techniques may be used for selecting the MAPs when the number of generated child MAPs is greater than the number of MAPs to be used for each generation (i.e., when the generation is overloaded). For example, in an embodiment, the MAPs for the next generation may be selected at random from the pool of generated children and then discarding the unselected MAPs. Or, for example, the fitting system may implement a strategy for selecting the MAPs, such as by placing relative weights on children from particular parents or on those from strictly selected parents. Or, for example, the number of MAPs may be reduced by the fitting system purposely selecting particular MAPs, such as to maintain maximum diversity between designs within a generation.

3. Tagging

Further, in embodiments, "tagging" may be employed to track and perform operations on good MAPs. Tagging refers to a mechanism for keeping track of particularly good MAPs. In an embodiment, a tag for a MAP may be stored, for example, in the memory of the fitting system. This tag may for example be stored as a numerical value, where the more preferred a MAP is the higher its tag value will be.

Various techniques may be used for identifying MAPs to be tagged. For example, in an embodiment, a MAP may be tagged if the patient quickly selects the MAP as a good MAP. For example, in an embodiment, a MAP may be tagged if the amount of time between when a sound token processed by the MAP is presented and when the patient selects the sound token processed by the MAP as good falls below a threshold time. Or, for example, MAPs may be tagged if the patient selects the MAP as a good MAP after only listening to the MAP less than a threshold number of times (e.g., once). Or, for example, if redundant child MAPs are generated within the same generation, the redundant child MAP may be tagged. It should be noted that these are but some exemplary techniques that may be used for identifying a particular MAP as preferred and increasing its tag value.

In an embodiment, tagging may be used to increase the likelihood that the children of a tagged parent are represented in the next generation. For example, if a parent is tagged, then the fitting system may use it a greater number of time in generating children. For example, if a MAP has a tag value of two, the MAP may be used twice in generating children. This will thus result in the children of tagged parents being represented in the pool of children twice as often as the children of non-tagged parents. Thus, if the fitting system, in culling the overloaded generation, randomly selects the children for the next generation from this pool of children, then the children of a tagged parent have a higher likelihood of being selected than the children of untagged parents. Similarly, if a MAP has a tag of three, it may be used three times in generating child MAPs, such that the child MAP of this MAP have three times the likelihood of being selected.

4. Amplification

As noted above, in an embodiment, a MAP may be tagged if it appears more than once in the pool of generated child MAPs. In such an embodiment, after tagging the redundant MAPs, all but one of each similar tagged MAP may be modified to create a new MAP unique to the current generation. In essence, redundantly produced MAPs are replaced to amplify the diversity within a generation. For instance, a four-MAP generation comprised of [11111], [11111], [00000], and [00000] has two different unique MAPs. MAPs [11111] and [00000] are tagged as being redundant, and a new amplified generation would comprise [11111], [00000], and two additional unique designs. The creation of the new unique MAPs can be accomplished several ways. They may be selected at random from the global population, as long as they are unique to the current generation. Alternately, the additional unique MAPs may be slightly altered versions of the redundant MAP. For example, all genes/parameters of tagged MAPs may be kept the same except one, which is modified so that a valid unique MAP is created. Following the example above, the original generation comprised of [11111], [11111], [00000], and [00000] may potentially be changed to [11111], [01111], [00000], and [00001]. The selection of which bit to modify may be a random decision or may be governed by a specific rule. One such rule may base the selection on visitation frequency. For instance, if over the course of the evolution, the first bit-place has never been a "1" but all others have been either a "1" or a "0" many times, a rule that favors infrequency would favor modifying the value in first bit-place. It should be noted that in another embodiment, rather than increasing the tag of a MAP if it appears more than once in a pool of child MAPs, the redundant MAPs may simply be replaced by new MAPs, such as discussed above. Further, in determining whether a MAP is redundant, the fitting system may ignore MAPs represented in the pool of children more than once as the result of the MAPs being the children of a tagged parent. It should be noted that the presently described example of tagging was discussed with reference to MAPs represented by bit strings for simplification of the explanation of tagging; and, in other embodiments tagging may be employed in embodiments using parameter based MAPs.

E. Exemplary Fitting System Arrangement

Figure 12:
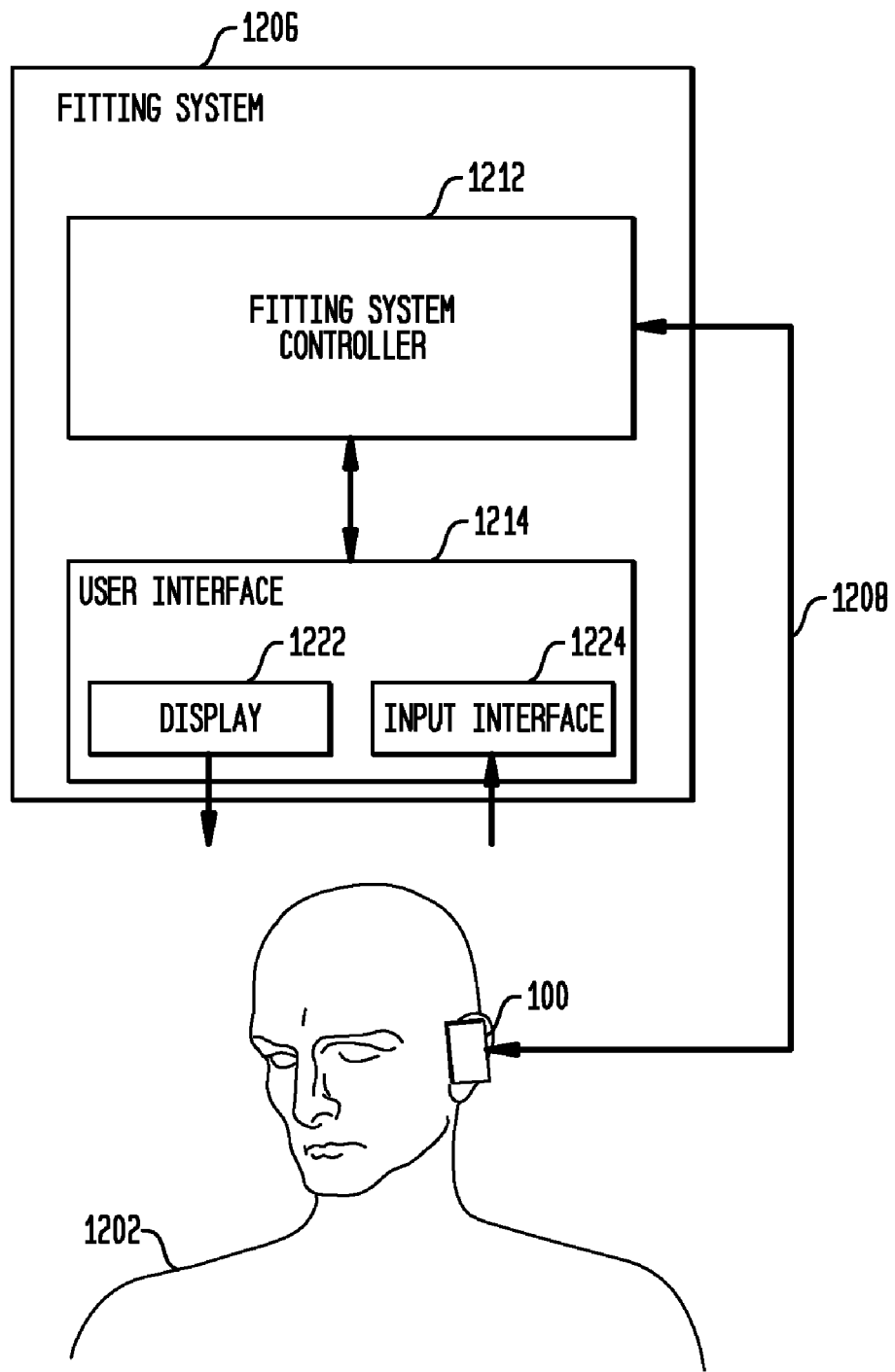
FIG. 12 is a schematic diagram illustrating one exemplary arrangement in which a patient operated fitting system may be used in fitting a cochlear implant system, in accordance with an embodiment.

FIG. 12 is a schematic diagram illustrating one exemplary arrangement 1200 in which a patient 1202 operated fitting system 1206 may be used in fitting a cochlear implant system 100, in accordance with an embodiment. In the embodiment illustrated in FIG. 12, speech processor 116 of cochlear implant system 100 may be connected directly to fitting system 1206 to establish a data communication link 1208 between the speech processor 116 and fitting system 1206. Fitting system 1206 is thereafter bi-directionally coupled by means of data communication link 1208 with speech processor 116. It should be appreciated that although speech processor 116 and fitting system 1206 are connected via a cable in FIG. 12, any communications link now or later developed may be utilized to communicably couple the implant and fitting system.

Fitting system 1206 may comprise a fitting system controller 1212 as well as a user interface 1214. Controller 1212 may be any type of device capable of executing instructions such as, for example, a general or special purpose computer, a handheld computer (e.g., personal digital assistant (PDA)), digital electronic circuitry, integrated circuitry, specially designed ASICs (application specific integrated circuits), firmware, software, and/or combinations thereof. Controller 1212 may further comprise an interface for establishing the data communications link 1208 with the cochlear implant 100. In embodiments in which controller 1212 comprises a computer, this interface may be for example, internal or external to the computer. For example, in an embodiment, controller 1206 and cochlear implant may each comprise a USB, Firewire, Bluetooth, WiFi, or other communications interface through which data communications link 1208 may be established. Controller 1212 may further comprise a storage for use in storing information. This storage may be for example, volatile or non-volatile storage, such as, for example, random access memory, solid state storage, magnetic storage, holographic storage, etc.

User interface 1214 may comprise a display 1222 and an input interface 1224. Display 1222 may be, for example, any type of display device, such as, for example, those commonly used with computer systems. Input interface 1224 may be any type of interface capable of receiving information from a patient, such as, for example, a computer keyboard, mouse, voice-responsive software, touch-screen (e.g., integrated with display 1222), retinal control, joystick, and any other data entry or data presentation formats now or later developed.

F. Exemplary Embodiment

Parameter Based MAPs

Figure 13:
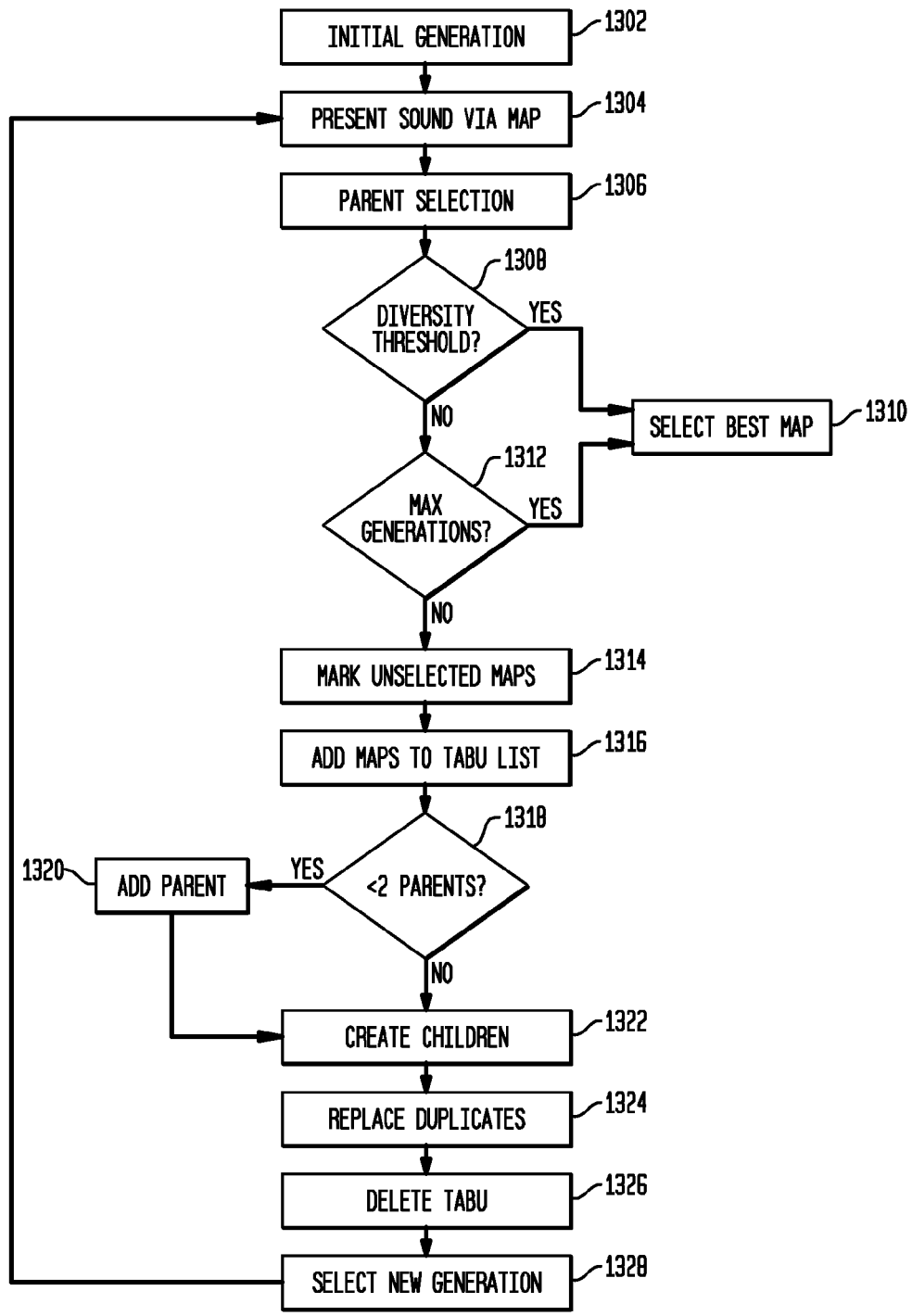
FIG. 13 is a flow chart of operations that may performed to determine a parameter map using a tabu search, in accordance with an embodiment.

FIG. 13 is a flow chart of operations that may be performed to determine a parameter map using a tabu search, in accordance with an embodiment. FIG. 13 will be described with reference to the above-discussed FIG. 12. Additionally, FIG. 12 will be discussed with reference to data structures in which the genetic algorithm modifies the actual parameters of the MAPs (i.e., parameter based MAPs) as opposed to implementations in which the genetic algorithm uses bit string representations of the MAPs. In such an implementation, a set of parameters and their possible values may be selected and used to define the data structure. These data structures may be defined, for example, by defining a class such as used in the C family of programming languages. The following provides an example of exemplary parameters that may be included in such a MAP data structure, as well as exemplary possible parameter values for the parameters (included in the brackets). It should be noted that these parameters and possible values are exemplary only, and provided for illustrative purposes.

| | |
|---|---|
| Strategy | [ ACE PACE ] |
| Channels | [ 6 8 10 12 14 16 18 20 22 ] |
| StimRate | [ 250 500 720 900 1200 1800 2400 ] |
| Maxima | [ 4 6 8 10 12 14 16 18 20 22 ] |
| Q | [ 10 15 20 25 30 35 40 ] |
| FATShift | [ 0 1 2 3 ] |
| Gain | [ LoCut LoBoost HiCut HiBoost AllCut AllBoost 2ndBoost Flat ] |

The Strategy parameter defines the type of speech coding strategy that the cochlear implant may implement, and in this example, the possible parameter values are either Advanced Combination Encoders (ACE), and Psychoacoustic Advanced Combination Encoders (PACE, commonly known as the MP3000 strategy). The Channels parameter specifies the number of stimulation channels that will be implemented by the cochlear implant, and in this example, the cochlear implant may implement, 6, 8, 10, 12, 13, 16, 18, 20, or 22 separate stimulation channels. The StimRate parameter specifies the stimulation rate to be used by the cochlear implant, and in this example, may be 250, 500, 720, 900, 1200, 1800, or 2400 pulses per second (pps). The Maxima parameter specifies the number of maxima to be used by the cochlear implant in providing stimulation, and in this example, may be 4, 6, 8, 10, 12, 14, 16, 18, 20, or 22 maxima. The Q parameter specifies the Q-factor for a loudness growth function used by the cochlear implant, and in this example, may be 10, 15, 20, 25, 30, 35, or 40. The FATShift parameter specifies the above-discussed FAT shift, and in this example, may be 0, 1, 2, or 3. The Gain parameter specifies the shape of a gain function to be applied to received audible signals, and in this example, may be LoCut (specifying a shape that de-emphasizes lower frequencies), LoBoost (specifying a shape that boosts lower frequencies), HiCut (specifying a shape that de-emphasizes higher frequencies), HiBoost (specifying a shape that boosts higher frequencies), AllCut (specifying a shape that de-emphasizes all frequencies), AllBoost (specifying a shape that boosts all frequencies), 2ndBoost (specifying a shape that boosts all frequencies by an amount greater than AllBoost), and Flat (specifying a shape that neither emphasizes nor boosts any frequencies).

Initially at block 1302, a generation of eight MAPs 200 is selected. It should be noted that this number need not be 8, but may vary depending on the implementation. Initialization involves the selection of the first generation of designs (i.e., MAPs). Various techniques may be used to select this initial generation of MAPs. For example, this selection may be performed by selecting at random from among the set of possible MAPs. Or, for example, in order to insure greater diversity among the selected initial generation of MAPs, the MAPs may be selected so that the each parameter value is represented in at least one MAP. For parameters in which the number of possible variables is greater than the number of MAPs in the initial generation, the values may be randomly selected such that each MAP in the initial generation has a unique value for the parameter. Moreover, pre-selected MAPs may also be included among the MAPs of the first generation. These pre-selected MAPs may be drawn, for example, from prior runs of the fitting procedure, MAPs stored in a memory of fitting system 1206, or MAPs selected by a clinician based on his experience, suggestions and recommendations from others, etc.

At block 1304, audible signals processed by the MAPs are presented to the patient. This may involve fitting system 1206 sequentially presenting an audible signal that that is processed using one of the MAPs to the patient. The audible signal may be a sound token, such as the above-discussed speech tokens. Further, in addition to being speech, in embodiments these sound tokens may be for any type other type of sound, such as a particular piece of music, or portion of same, a musical instrument, a car horn, etc. These audible signals (e.g., sound tokens) may be stored in a file contained in a library of sound tokens stored, for example, in the fitting system 1206 or fitting system 1206 may access an external system storing the sound tokens.

In an embodiment, fitting system 1206 may randomly select a sound token for each of the 8 MAPs. Fitting system 1206 may then download the MAP corresponding to a particular sound token to the cochlear implant, and then play the audible signal (e.g., the sound token). This audible signal may be played using, for example, one or more speakers connected to fitting system 1206, such as, for example, a set of headphones worn by the patient 1202. Further, patient 1202 and fitting system 1202 may be located in a room designed to minimize external noise signal interfering with the presentation of the audible signal, such as, for example, a sound proof room. Or, for example, fitting system 1206 may provide the audible signal directly to cochlear implant 100 via data communications link 1208. After fitting system 1206 presents the first sound token to the patient 1202, the fitting system 1206 may download the next MAP to the cochlear implant 100 and then play the corresponding sound token to the patient 1202. This process may then continue sequentially until fitting system 1206 presents sound tokens processed by all 8 MAPs to the patient 1202. In yet another embodiment, rather than downloading each MAP to cochlear implant 100, fitting system 1206 may process the sound tokens using the MAPs to determine the data for use in generating the stimulation signals to be presented to the patient via the electrode array, and fitting system 1206 may provide this data to the cochlear implant 100 via data communications link 1208. Or, in yet another embodiment, fitting system 1206 may download the MAP to cochlear implant 100. Then, cochlear implant 100 may process sound from the general audio environment received via the microphone(s) of cochlear implant 100 using the downloaded MAP. In other words, in this alternative embodiment, fitting system 1206 does not present sound tokens to the patient; but instead, cochlear implant 100 simply processes audible signals received by the microphone, such as the voice of someone speaking to them, their television at home, etc. Thus, although the presently described embodiment is discussed with reference to sound tokens being presented to the patient that are processed by the MAPs, it should be understood that in other embodiments, the audible signals processed by the MAPs and presented to the patient need not be sound tokens, but may be other types of audible signals such as any audible signals received by the microphone(s) of the cochlear implant.

After fitting system 1206 presents each of the sound tokens and corresponding MAPs to the patient 1202, fitting system 1206 may then receive an indication from the patient 1202 regarding which sound tokens were perceived as good by the patient 1202. Using this indication, fitting system 1206 may determine the parents for the next generation of MAPs at block 1306. For example, in an embodiment, all MAPs identified as good by the recipient may be selected as parent MAPs for generating the next generation of MAPs.

1. Variable Selection—Exemplary GUI

Figure 14:
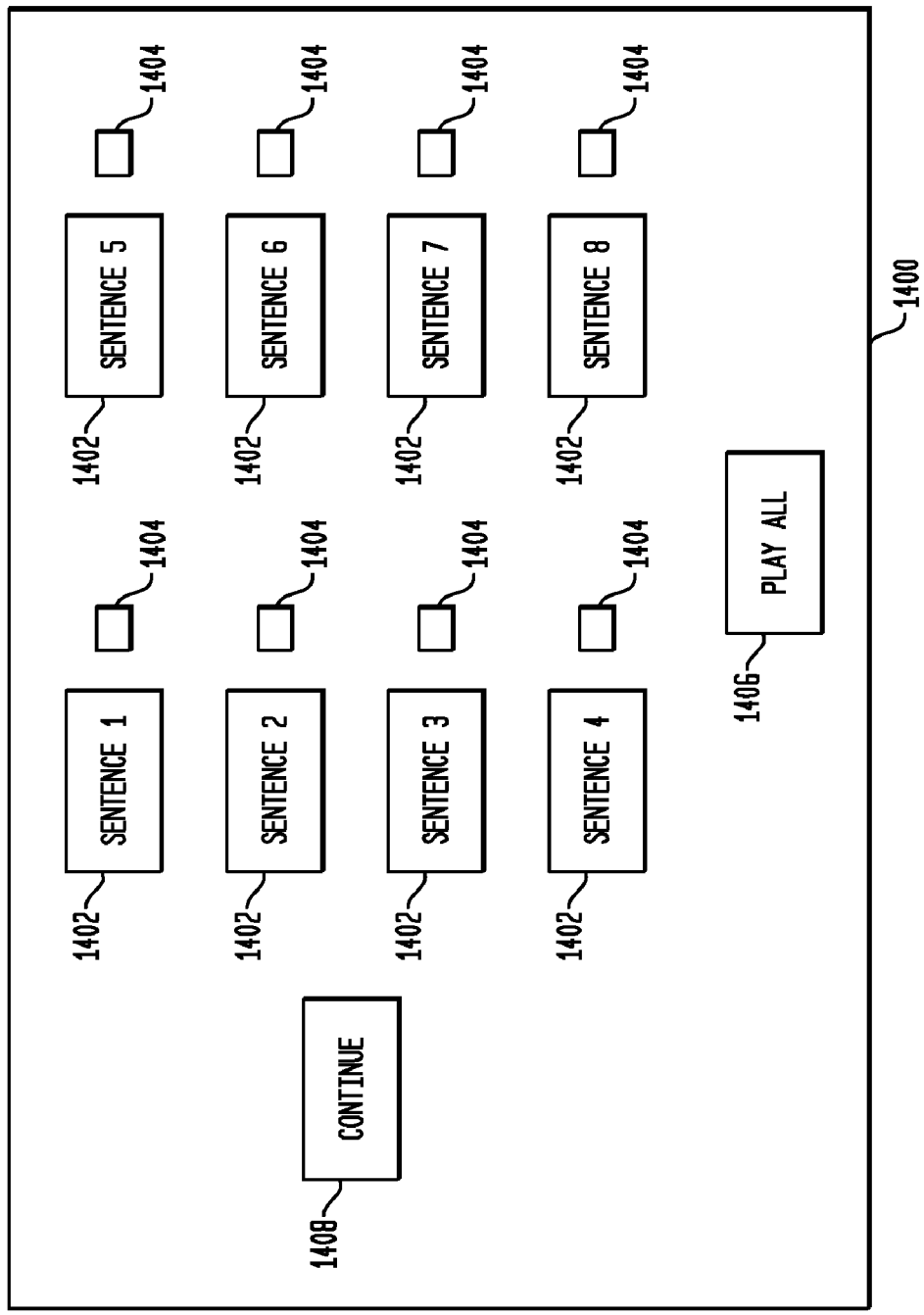
FIG. 14 provides an exemplary user interface that a fitting system may present to the patient to obtain a patient response, in accordance with an embodiment.

FIG. 14 provides an exemplary user interface 1300 that fitting system 1206 may present to the patient 1202 to obtain the patient's response. User interface 1300 may be presented on display 1222 and the patient may use input interface 1222 to provide the response. In this example, 8 sound tokens each processed with a corresponding MAP are presented to the patient 1202. As illustrated, an icon 1402 and a corresponding check box 1404 is displayed for each of the presented sentences. The patient 1202 may, for example, click on the icon 1402 corresponding to a particular presented sound token to direct fitting system 1206 to replay the corresponding sound token to the patient 1202 with the corresponding MAP. If the patient desires to hear all the sound tokens, the patient 1402 may select a replay all icon 1406 to direct fitting system to sequentially present each of the sound tokens and their corresponding MAPs to the patient 1202. Additionally, in an embodiment, the icon 1402 corresponding to the presented sound token may change in appearance while the sound token is being played, such as, for example, by changing the icon's 1402 color, shape, size, etc.

The patient 1202 may then check the check box 1404 corresponding to a particular sound token to indicate that the patient 1202 considered the sound token to be good. When the patient has made their selections, the patient 1202 may select the continue icon 1408 to direct the fitting system 1206 to save the selections and use the MAPs corresponding to the selected sound tokens as parents for generating the next generation of children.

Because in this example, the patient 1202 may select any number of sound tokens as good (e.g., between 0 and 8), the number of generated children may vary. For example, if no sound tokens or only 1 sound token is selected as good, there are not two selected parents and thus no generated children. In such a situation, the fitting system 1206 may select new sound tokens but use the previous generation of MAPs to present the new sound tokens to the patient 1202. If, however, a predetermined number of consecutive presentations of sound tokens to the patient results in no or only one MAP being selected as good, the process may be restarted (i.e., return to block 1302) and an entirely new set of MAPs randomly generated for subsequent processing using the genetic algorithm.

Additionally, in an embodiment, it may be desirable that an even number of parent MAPs be used for generating children MAPs. In such an embodiment, if the patient selects an odd number of MAPs, fitting system 1206 may add an additional MAP to the set of parent MAPs. Various techniques may be used for selecting this additional MAP, such as randomly selecting a MAP that has not yet been used, selecting a MAP based on the tag value of MAPs, etc.

In an embodiment, fitting system 1206 may also tag any MAPs that are determined to be particularly good. For example, the fitting system 1206 may increase the stored tag value for a MAP if the patient 1202 checks the check box 1404 for the sound token corresponding to the MAP within a particular period of time after the sound token is presented, or, for example, if the check box 1404 is checked after listening to the sound token less than a particular number of times (e.g., after listening to the sound token only once). As noted above, the tag values from tagged MAPs may be stored in the memory of fitting system 1206.

Further, in an embodiment, fitting system 1206 may also store information regarding which MAPs were selected, which MAPs were not selected, as well as the generation number in which the MAP was selected or not, the parent MAPs used to generate the particular MAP, etc. This information may be stored, for example, in a table stored in a storage of fitting system 1206.

It should be noted that FIG. 14 is but one example of a user interface 1400 that fitting system 1206 may present to a patient to obtain the patient's response to the presented sound tokens processed by the MAPs and in other embodiments other mechanisms may be used to present audible signals processed by the MAPs to the patient and obtain the patient's response. For example, in an embodiment, a user interface may be used such as discussed below with reference to FIG. 15 may be used.

2. Search Diversity as a Stopping Criteria

Referring back to FIG. 13, after the parent MAPs are selected, fitting system 1206 checks to see if a diversity threshold has been reached at block 1308 for the selected MAPs. If the diversity threshold is met then the surviving MAPs are the final MAPs that are processed as described herein. This diversity may be, for example, the diversity of the genetic algorithm search, or for example, the diversity of the selected MAPs, such as discussed above. In embodiments in which the diversity of the genetic algorithm is used as a stopping criterion, the fitting system 1206 may use various techniques for determining whether this diversity threshold has been met. For example, fitting system 1206 may determine whether a particular threshold of all MAPs have been presented to the patient (i.e., MAPs that are used to process audible signals presented to the patient processed by the MAPs). In one such embodiment, the fitting system may determine that sufficient diversity has been achieved if a particular percentage (e.g., 5%) of all possible valid MAPs have been presented to the patient in block 1304 (i.e., MAPs that are used to process audible signals presented to the patient processed by the MAPs). Or, for example, fitting system 1206 may compute whether each possible parameter value for each parameter has been used in the MAPs used to process sound tokens presented to the patient at block 1304. Or, for example, whether a particular percentage of possible values for each of one or more, or all parameters has been used in the MAPs used to process sound tokens presented to the patient. In determining whether the genetic algorithm is sufficiently diverse, fitting system 1206 may retrieve information stored by the fitting system 1206 regarding the MAPs used to process sound tokens presented to patient and the parameter values for these MAPs. It should be noted that these are but some exemplary techniques that fitting system 1206 may use for determining whether the genetic algorithm search is sufficiently diverse and other techniques may be used for determining at block 1308 whether a specified diversity of the genetic algorithm has been achieved. It should be noted that although using the diversity of the genetic algorithm search as a stopping criteria is discussed in this embodiment involving the use of parameter based MAPs, the diversity of the genetic algorithm search may be used as a stopping criteria in other embodiments, such as those discussed above that use bit string representations of the MAPs.

If sufficient diversity has been achieved, fitting system 1206 may then determine, at block 1310, the particular MAP to be used by the cochlear implant 100 and download this determined MAP to cochlear implant 100 for subsequent use. Various techniques may be used for determining the final MAP, such as, for example, by presenting sound tokens processed by each of the final selected MAPs to the patient 1202 and receiving an indication from the patient regarding which MAP is considered the best MAP. The term final MAP is used in this description to refer to the MAP that is determined by the genetic algorithm and subsequently downloaded to the cochlear implant 100 for use after fitting the implant. However, it should be noted that this MAP may be changed after fitting, such as, for example, the patient 1202 re-fitting the cochlear implant 100 at a later time. Further, prior to downloading the final MAP to cochlear implant 100, fitting system 1206 may store the final MAP in, for example, a patient specific gallery of MAPs. This gallery may be, for example, stored in storage within fitting system 1206 or an external storage device 1206.

In another embodiment, the final MAP may be selected by fitting system 1206 computing a Simpson Diversity Index (SDI) for each parameter in each generation to create an SDI Matrix (#parameters×#generations), and identifying which parameters the patient does not have a strong preference for. As noted above, fitting system 1206, during each iteration of the process, may store information regarding each MAP used to process sound tokens presented to the patient. Fitting system 1206 may use this stored information regarding the MAPs to identify which parameters the patient does not have a strong preference for. For example, fitting system 1206 may identify which parameters the patient does not have a strong preference for by, for example, fitting system 1206 determining the mean of the SDI values for each parameter column across all generations, and identifying as insensitive parameters for which the mean SDI value is over 50%. It should be noted that 50% was selected for explanatory purposes and different percentages may be used in other implementations. Next, fitting system 1206 may identify the MAPs that were selected most often, such as, for example, the MAPs that were selected most often (e.g., the 4 most selected MAPs). In doing so, fitting system 1206 may ignore any parameters determined to be insensitive. Fitting system 1206 may then present sound tokens processed by each of these MAPs to the patient 1202 who then selects the MAP that the patient determines is best.

In presenting sound tokens processed by the final round of MAPs to the patient, fitting system 1206 may provide multiple rounds of presentations, where each MAP is used in each round using a different sound token. The patient 1206 may then select the "best" MAP for each round, and then after a particular number of rounds (e.g., 4 rounds), the MAP that was selected as best the most amount of times is determined to be the final MAP. If after 4 rounds, there is a tie, a series of one or more rounds may be run for the top tied MAPs to determine the final MAP.

If at block 1308, the diversity threshold has not been achieved, fitting system 1206 may determine if the maximum number of generations has been achieved at block 1312. If so, fitting system 1206 may proceed to block 1310 to select the final MAP. Otherwise the algorithm continues to block 1314. Fitting system 1206 may determine if the maximum number of generations has been reached by maintaining a tally of each pass through block 1312 and then comparing this tally against a particular value specifying the maximum number of generations to be used in determining the final MAP.

In another embodiment, rather than checking if sufficient diversity has been achieved (block 1308) and whether the maximum number of generations has been reached (block 1312), the patient may be presented via a user interface with an option of selecting to end the process or not. The process of FIG. 13 may then continue until the patient selects to end the process. After which, fitting system 1206 determines the final MAP and downloads this final MAP to the patient at block 1310.

At block 1314, fitting system stores an indication in its memory for each MAP that was not selected. If a MAP has not been selected two or more times, fitting system 1206 adds that MAP to a tabu list, which fitting system 1206 may store in its memory. It should be noted that this is but one example of how fitting system 1206 may keep track of tabu MAPs, and other mechanisms may be used, such as those discussed above.

At block 1318, fitting system 1206 may check to see if the patient 1202 selected two or more MAPs at block 1306. If not, fitting system 1206 may add new MAPs to the pool of MAPs to be used as parents at block 1320. Various techniques may be used for adding these new MAPs. For example, fitting system 1206 may add the MAPs from a previous generation, such as the immediately preceding generation to the pool of parent MAPs. Or, for example, fitting system 1206 may add randomly selected MAPs to the pool of parents. Or, fitting system 1206 may add one or more, or all, previously tagged MAPs to the pool of parents. Or, alternative mechanisms may be used to increase the number of MAPs in the pool of parents to two or more MAPs (or some other particular number).

Fitting system may then generate child MAPs at block 1322. Various techniques may be used for generating the child MAPs, such as those discussed above. For example, fitting system may use multiple cut points, mutations, freezing, adding tagged parents to the pool of children, including multiple child MAPs of tag parents, etc. to the pool of generated children. For example, fitting system 206 may mutate the children MAPs generated at block 1322 by applying a mutation rate to each parameter of the generated child MAPs to determine whether or not to mutate the parameter. Typically this mutation rate (probability) may range from 1 to 10%. In one embodiment, the mutation probability is approximately 3%. Then, if fitting system 206 determines to mutate a particular parameter, fitting system 206 mutates the parameter, such as by changing the parameter to a randomly selected parameter. Further, if a particular parameter was previously determined to be frozen, fitting system 206 does not mutate the parameter, and, as such, does not apply the mutation rate to the parameter, in an embodiment.

3. Overloaded Generations

In an embodiment, fitting system 1206 may generate child MAPs by pairing each selected MAP with every other selected MAP using every possible cut point. That is, if MAPs A, B, C, and D are selected, then child MAP may be generated for each of the following pairings: A-B, A-C, A-D, B-C, C-D, and C-D, using each possible cut point for each pairing. This, accordingly, may result in a large number of child MAPs and thus an overloaded generation.

4. Tagging and Amplification

If there are any duplicate MAPs in the pool of generated children, fitting system 1206 may tag these redundant MAPs at block 1324. Additionally, fitting system 1206 may replace the redundant MAP (or MAPs if there are three or more identical child MAPs) with a mutated version of the MAP, such as was discussed above. For example, fitting system 1206 may replace one or more parameter values in all but one of the redundant MAPs with a different parameter value. These new parameter values may be randomly selected or selected based on whether the parameter value has yet been used in a MAP used in processing a sound token presented to the patient 1202. For example, as noted above, in an embodiment, fitting system 1206 may store information regarding each MAP that is used to process a sound token presented to the patient 1202. Fitting system 1206 may then consult this stored information in determining how to replace a redundant MAP. For example, if a particular parameter value has not yet been used in a MAP used to process a sound token presented to the patient, the fitting system 1206 may replace one or more of the redundant MAPs with a MAP including this parameter value. Or, for example, rather than replacing redundant MAP with a mutated version of the MAP, in other embodiments, a redundant MAP may be replaced with a randomly selected MAP, a MAP that has not yet been used to process a sound token presented to the patient, a tagged MAP, etc.

5. Tabu List

If any of the generated child MAPs are on the tabu list, fitting system 1206 may delete these children at block 1326. For example, fitting system 1206 may examine the stored tabu list to determine if any of the child MAPs are included in the tabu list, and, if so, delete these children from the pool of MAPs. Fitting system 1206 may also delete any invalid child MAPs at block 1326, such as, for example, if a child MAP is generated where the number of maxima for the MAP is greater than the number of channels specified for the MAP.

Fitting system 1206 then, at block 1328, selects from this pool of child MAPs the next group of MAPs to be used for processing sound tokens presented to the patient. Various techniques, such as those discussed above, may be used for selecting the surviving generation of MAPs. For example, in an embodiment, fitting system 1206 may randomly select a particular number (e.g., 8) MAPs from this pool of child MAPs, and use these 8 randomly selected MAPs as the surviving child MAPs. In an embodiment, it may be desirable that the number of children MAPs selected at block 1328 be an even number. Further, in an embodiment, it may be desirable that pairs of children MAPs are selected for the next generation of MAPs. A pair of children MAPs refers to the two children MAPs generated from a particular combination of parent MAPs using a particular cut point. For example, referring back to FIG. 2B, the two parent MAPs 222 and 224 ([01100100] and [10110111]) using a cut point after the $4^{th}$ bit result in a child MAP 226 [10110100] and a child MAP [01100111] (not shown). These two children MAPs come from the same set of parent MAPs using the same cut point, and are thus referred to herein as paired children MAPs. It should be noted that although the above description of paired children MAPs is provided with reference to bit string representations of MAPs, this was provided to simplify the explanation of paired children MAPs, and the same concept applies to paired children MAPs where the MAPs are represented by data structures, such as presently discussed with reference to the embodiment of FIG. 13. In an embodiment in which 8 MAPs are to be selected as the children MAPs, fitting system 1206 may randomly select 4 MAPs from the pool of surviving children MAPs and then add the pairs for these selected MAPs to select the 8 MAPs for the next generation.

Fitting system 1206 may then return to block 1304 and present sound tokens processed by these surviving child MAPs to the patient. The process may then continue until either sufficient diversity is achieved at block 1308 or the maximum number of generations is reached at block 1312.

In yet another embodiment, rather than the fitting system 1206 asking the patient 1202 whether the sound perception was good or not, the fitting system 206 may ask the patient 1202 what they heard. And, then fitting system 1206 may identify the corresponding MAP as good if the patient 1202 correctly identifies the sound token. For example, in an embodiment, the sound tokens may comprise spoken phrases. Then, fitting system 1206 may present a graphical user interface (GUI) to the patient 1202 via display 1222 that lets the patient 1202 select a graphical list of possible phrases. If the patient 1202 selects the correct phrase, the corresponding MAP may be deemed good, while if the incorrect phrase was selected, the corresponding MAP may be deemed bad. That is, if the correct phrase is identified, fitting system 1206 may select the corresponding MAP at block 1306. While, if the correct phrase is not identified, fitting system 1206 may not select the corresponding MAP at block 1306.

G. Alternative Exemplary GUI

Figure 15:
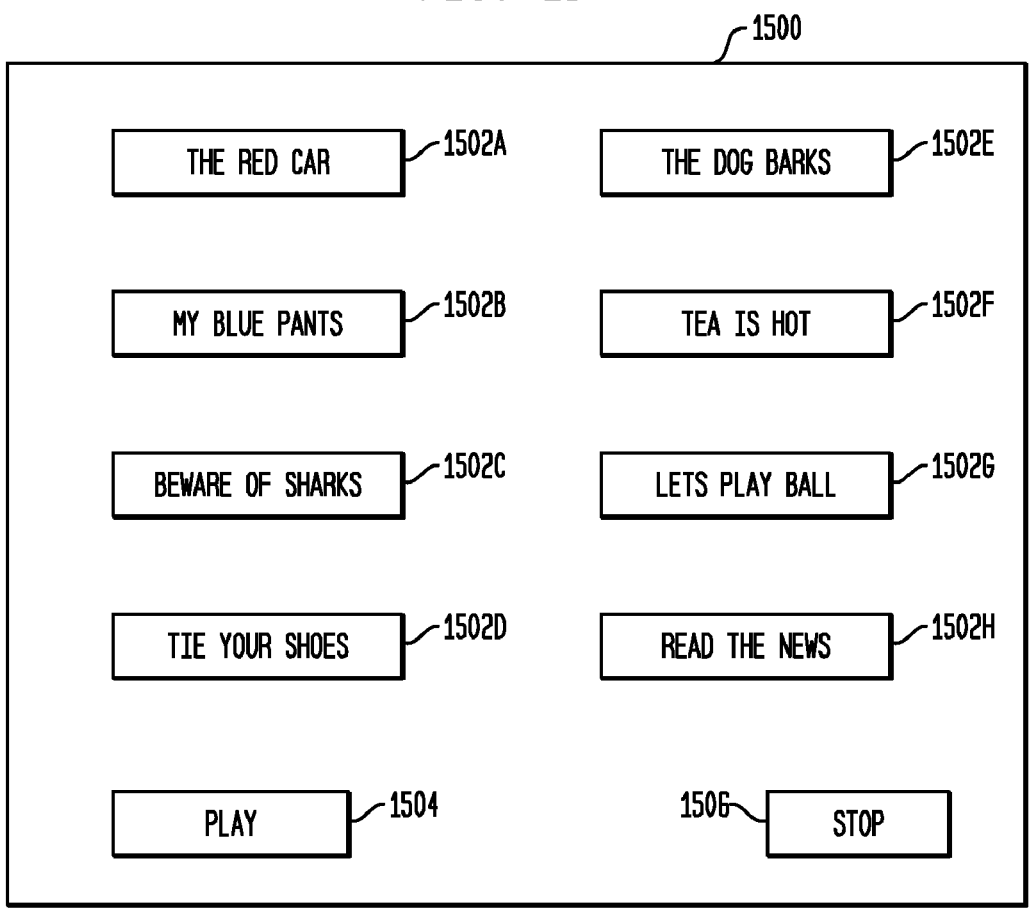
FIG. 15 illustrates an exemplary GUI that may be provided to a patient for obtaining the patients perception of applied stimulation, in accordance with an embodiment.

FIG. 15 illustrates an exemplary GUI 1500 that may be provided to a patient 1202 for obtaining the patients selection of parent MAPs at block 1306, in accordance with an embodiment. As illustrated, GUI 1500 may comprise a set of icons 1502 that the patient 1202 may select to indicate which phrase they believe they heard. For example, these icons 1502 may include an icon for selecting that the patient 1202 heard any one of eight phrases 1502A-H. This GUI 1500 may be displayed on display 1222. The patient 1202 may, using input interface 1224, select the icon 1502 corresponding to the phrase they believe they heard. The input interface 1224 may then provide this response to fitting system controller 1212.

Additionally, GUI 1500 may include a play icon 1504 that the patient 1202 may select to direct the fitting system controller 1212 to play the phrase that the patient 1202 is to identify. The GUI 1500 may also comprise a stop button 1506 that the patient 1202 may select to stop the process, such as if the patient 1202 needs to leave for any purpose.

It should be noted that GUI 1500 is exemplary only and provided to illustrate one example of a GUI interface that may be used for determining whether a patient can correctly identify a sound token processed by a particular MAP. For example, in other embodiments, the sound token may be a sound from a musical instrument and the icons that the patient 1202 may select may be in the shape of different instruments and/or be identified by the name of a particular instrument. Further, in other embodiments, the patient 1202 may be able to use check boxes, pull-downs, or other mechanisms for identifying a particular sound.

In an embodiment in which the patient 1202 is asked to correctly identify a particular sound, the fitting system 1206 may sequentially present sound tokens processed by a predetermined number of MAPs (e.g., 8) to the patient each processing a different sound token. Then, the MAPs corresponding to sounds that the patient correctly identified are deemed by the fitting system 1206 as good and accordingly selected at block 1306. As such, in this example, the number of MAPs selected at block 1306 may vary between 0 and all of the MAPs used to process the presented sound tokens. In the event no MAPs are selected at block 1306, the process may return to block 1306 and the previously set of MAPs may be represented to the patient 1202, although this time with a new set of sound tokens. If, however, no MAPs are again selected at block 1306, the process may be re-started and returned to block 404.

In yet another embodiment, the steps of blocks 1304 and 1306 may be repeated until the patient correctly identifies a particular number of sound tokens. Then, fitting system 1206 may select as parents the MAPs corresponding to the correctly identified sound tokens. For example, in an embodiment, fitting system 1206 may randomly select a child MAP from the child MAPs generated at block 1328 and then present sound tokens processed by the selected MAP to the patient 1202. The fitting system 1202 may then ask the patient 1202 to correctly identify a sound token processed using the MAP. After which, fitting system 1206 may randomly select another child MAP and present a sound tokens processed by this MAP to the patient. This process may then continue until the patient correctly identifies a particular number of sound tokens (e.g., 4). The fitting system 1206 may then use the MAPs corresponding to the correctly identified sound tokens as the parent MAPs selected at block 1306.

In yet another embodiment, the patient may be able to rank each presented sound token processed by a MAP. For example, fitting system 1206 may present the patient with a GUI that allows the patient to rank how well they perceived the played sound. For example, GUI 1500 may include a series of checkboxes that the patient may select to rank how well they thought the MAP performed. These checkboxes might include checkboxes for the following rankings: great, good, average, below average, poor. It should be noted that this is but one example of how a fitting system may be able to rank the performance of MAPs, and other mechanisms may be used. In an embodiment, the ranking assigned by the patient 1202 may be used to increase a corresponding tag associated with the MAP.

In certain embodiments, certain sound tokens may work better with other MAPs or certain sound tokens may be simply difficult for the patient to understand regardless of the MAP used to process the sound token. For example, if a sound token comprises speech from a person with a strong southern accent, but the patient 1202 speaks with a strong English accent, the sound token may be difficult for the patient to identify regardless of the MAP. Thus, it is possible that good MAPs may not be selected at block 1306 if they are paired with a bad sound token. In order to mitigate the impact of bad sound tokens, in an embodiment, blocks 1304 and 1306 may be repeated two or more times. For example, in a first pass through blocks 1304 and 1306, each MAP may be paired with a particular sound token. Then, during the second pass, the same MAPs and sound tokens may be used, but with different sound tokens matched up with different MAPs. For example, in an embodiment, in the second pass, the MAPs considered bad in the first pass may switch sound tokens with the MAPs considered good in the first pass. As an illustrative example, in a first pass MAP "A" processes token "1," "B" processes token "2," "C" processes token "3", "D" processes token "4", "E" processes token "5," "F" processes token "6," "G" processes token "7," and "H," processes token "8." Then, if MAPs A, B, C, and D are selected, in the next pass through blocks 1304 and 1306 MAP A may be paired with token 5, B with token 6, C with token 7, D with token 8, E with token 1, F with token 2, G with token 3, and H with token 4. Then, at block 1306, in the second pass through, fitting system 1206 may identify any MAP selected in either pass as good and use these MAPs as parents for generating the next generation.

The above discussed process of FIG. 13-15 may be embodied on software executable by any device capable of executing instructions, such as a computer (e.g., a personal computer, a handheld computer (e.g., a PDA, a smartphone, a wireless device with a processor, etc.). For example, in an embodiment fitting system 1206 may be a patient's home computer on which such software is loaded. Additionally, in such an embodiment, a piece of hardware may be used for allowing the patient's computer to communicate with the patient's cochlear implant for the purposes of, for example, changing the MAP used by the patient's cochlear implant. This hardware may be connected to the patient's computer using for example, as USB interface, a firewire interface or any other suitable mechanism. Or, for example, the patient's computer may communicate wirelessly with the patient's cochlear implant using Wi-Fi, Bluetooth, or any other suitable wireless interface included in the computer and cochlear implant. Additionally, in embodiments, the patient could perform optimizations at using signals of his or her own choosing (e.g., a spouse's voice, a musical piece, etc.). In such embodiment, the software may provide the patient with the ability to upload and store these audible signals for use by the genetic algorithm.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A computer-implemented method for at least partially fitting a medical implant system to a patient comprising:
   executing a genetic algorithm to select a determined value set comprising values for a plurality of fitting parameters, the genetic algorithm comprising:
      presenting signals processed by a plurality of value sets to the patient using the medical implant system;
      receiving patient feedback in response to the presented signals processed by the plurality of value sets;
      selecting, based on the patient feedback, one or more of the value sets;
      storing information, based on patient feedback, regarding one or more value sets that are to be excluded; and
      generating, via a computer, one or more successive generations of value sets using said selected one or more value sets; wherein said stored information is used to exclude one or more value sets from said successive generations; and
   providing said determined value set to said medical implant system for use in providing stimulation to the patient.

2. The method of claim 1, wherein storing information regarding one or more value sets that are to be excluded comprises:
   adding a value set that is to be excluded to a stored tabu list.

3. The method of claim 1, wherein:
receiving patient feedback comprises:
   receiving an indication from the patient that that one or more of the value sets are to be excluded; and
   storing information regarding one or more value sets that are to be excluded comprises:
      storing information regarding the value sets for which an indication was received that the value set is to be excluded.

4. The method of claim 1, wherein presenting signals processed by a plurality of value sets comprises:
   presenting a set of signals to the patient, wherein each of said presented signals is processed by the medical implant system using a corresponding value set.

5. The method of claim 4, wherein:
receiving patient feedback comprises:
   receiving an indication that one or more of the presented signals are perceived as good by the patient; and
   selecting one or more of the value sets comprises:
      selecting one or more value sets based on receiving an indication that the audible signal corresponding to the value set was perceived as good by the patient.

6. The method of claim 5, wherein storing information regarding one or more value sets that are to be excluded comprises:
   storing information indicating that a value set is to be excluded if an indication is not received that the signal corresponding to the value set was perceived as good in response to presenting the signal to the patient using the value set.

7. The method of claim 6, wherein storing information indicating that a value set is to be excluded, comprises:
   storing the information indicating that the value set is to be excluded in response to the value set being used to process two or more separate signals for which an indication is not received indicating that the patient perceived the signal as good.

8. The method of claim 6, further comprising:
   eliminating a value set from one or more successive generations if information is stored indicating the value set is to be excluded.

9. The method of claim 1, wherein:
the value sets are stored using a data structure in which the values for the parameters for the value set are stored, and generating one or more successive generations comprises:
   copying one or more values from a parent value set to generate a data structure storing a child value set.

10. The method of claim 1, wherein:
the value sets are represented by a string of bits; and
generating one or more successive generations comprises:
   copying one or more bits from a bit string for a parent value set to generate a bit string for a child value set.

11. The method of claim 1, wherein executing the genetic algorithm further comprises:
   determining whether a value set is included two or more times in a set of child value sets generated in a successive generation.

12. The method of claim 11, wherein the genetic algorithm further comprises:
   replacing at least one child value set that is included two or more times in a set of children value sets with an alternative value set.

13. The method of claim 12, wherein the alternative value set is selected from the set of a mutated version of the replaced value set, a randomly selected value set, and a value set not yet presented to the patient.

14. The method of claim 1, wherein generating one or more successive generations of value sets comprises:
   generating a number of child value sets wherein the number of generated child value sets is greater than the number of value sets presented when in presenting signals processed by a plurality of value sets to the patient;
   selecting a number of value sets from the child value sets wherein the number of selected child value sets is equal to the number of value sets presented to the patient.

15. The method of claim 1, wherein:
the genetic algorithm further comprises:
   storing a preference value for a value set; and
   generating one or more successive generations comprises:
      generating at least one child value set based on the value set for which the preference value is stored; and
      the stored preference value is used to increase the likelihood of the child value set being used in a subsequent presentation of a plurality of value sets to the patient.

16. The method of claim 15, wherein:
the genetic algorithm further comprises:
determining whether a value set is included two or more times in a set of child value sets generated in a successive generation; and
storing a preference value for a value set comprises:
increasing the preference value for a value set if the value set is determined to be included two or more times in a set of child value sets.

17. The method of claim 15, wherein storing a preference value for a value set comprises:
increasing the preference value for a value set based on the received patient feedback.

18. The method of claim 17, wherein increasing the preference value for a value set based on the received patient feedback comprises:
increasing the preference value for a value set if the patient identifies the value set as a good value set within a specified amount time after presenting the value set to the patient.

19. The method of claim 17, wherein:
presenting signals processed by a plurality of value sets to the patient comprises:
presenting a value set to the patient based on receiving a request from the patient to be presented with the value set;
increasing the preference value for a value set based on the received patient feedback comprises:
increasing the preference value for a value set if the patient identifies the value set as a good value set after being presented with the value set less than a specified number of times.

20. The method of claim 1, wherein the generic algorithm further comprises:
determining whether a specified diversity of the genetic algorithm has been reached; and
repeating the steps of presenting, receiving, selecting, storing, and generating until it is determined that the specified diversity has been reached.

21. The method of claim 20, wherein determining whether a specified diversity has been reached comprises:
determining whether the number of value sets presented to the patient exceeds a threshold.

22. The method of claim 21, wherein the threshold is based on a percentage of possible value sets for the medical implant system.

23. The method of claim 21, wherein the threshold is based on a particular percentage of possible values for one or more of the plurality of fitting parameters included in the value sets.

24. The method of claim 1, wherein the medical implant system is a cochlear implant system and wherein the signals are audible signals.

25. A system for at least partially fitting a medical implant system to a patient comprising:
a processor configured to execute a genetic algorithm to select a determined value set comprising values for a plurality of fitting parameters, the genetic algorithm comprising: presenting signals processed by a plurality of value sets to the patient using the medical implant system, receiving patient feedback in response to the presented signals processed by the plurality of value sets, selecting, based on the patient feedback, one or more of the value sets, storing information, based on patient feedback, regarding one or more value sets that are to be excluded, and generating one or more successive generations of value sets using said selected one or more value sets, wherein said stored information is used to exclude one or more value sets from said successive generations;
a storage configured to store the information regarding one or more value sets that are to be excluded; and
an interface configured to provide at least one of the value sets to the medical implant system for use by the medical implant system in providing stimulation to the patient.

26. The system of claim 25, wherein the processor is configured to add a value set that is to be excluded to a tabu list stored in said storage.

27. The system of claim 25, further comprising:
a user interface configured to receive the patient feedback.

28. The system of claim 25, further comprising:
one or more speakers configured to present a set of signals to the patient, wherein each of said presented signals is processed by the medical implant system using a value set; and
a user interface configured to receive the patient feedback, wherein the patient feedback comprises an indication from the patient regarding a patient perception of each of the presented signals; and
wherein the processor in selecting, based on patient feedback, one or more of the value sets is configured to select one or more value sets using the received indication.

29. The system of claim 28, wherein:
the user interface in receiving an indication from the patient is configured to receive an indication that one or more of the presented signals are perceived as good by the patient; and
the processor in selecting said value sets is configured to generate one or more child value sets for a successive generation using one or more of the value sets for which said good indication was received.

30. The system of claim 29, wherein the processor is further configured to store information in the storage indicating that a value set is to be excluded if an indication is not received that the signal corresponding to the value set was perceived as good in response to presenting the signal to the patient using the value set.

31. The system of claim 30, wherein the processor is further configured to store the information indicating that the value set is to be excluded in response to the value set being used to process two or more separate signals for which an indication is not received indicating that the patient perceived the signal as good.

32. The system of claim 31 wherein the processor is further configured to eliminate a value set from said one or more successive generations if information is stored indicating the generated value set is to be excluded.

33. The system of claim 25, wherein the storage stores the value sets using a data structure in which the values for the parameters for the value set are stored, and wherein said processor is configured to copy one or more values from a parent value set to generate a data structure storing a child value set.

34. The system of claim 25, wherein the value sets are represented by a string of bits; and wherein the storage stores information for corresponding the string of bits with a set of parameter values; and wherein the processor in generating one or more successive generations is configured to copy one or more bits from a bit string for a parent value set to generate a bit string for a child value set.

35. The system of claim 25, wherein the processor is further configured to determine whether a value set is included two or more times in a set of child value sets generated in a successive generation.

36. The system of claim 35, wherein the processor is further configured to replace at least one child value set that is included two or more times in a set of children value sets with an alternative value set.

37. The system of claim 36, wherein processor is configured to select the alternative value set from the set of a mutated version of the replaced value set, a randomly selected value set, and a value set not yet presented to the patient.

38. The system of claim 25, wherein the processor in generating one or more successive generations of value sets is configured to generate a number of child value sets wherein the number of generated child value sets is greater than the number of value sets presented when presenting signals processed by a plurality of value sets to the patient, and select a number of value sets from the child value sets wherein the number of selected child value sets is equal to the number of value sets presented to the patient.

39. The system of claim 25, wherein the processor is further configured to: store a preference value for a value set; generate at least one child value set based on the value set for which the preference value is stored in generating one or more successive generations; and use the stored preference value to increase the likelihood of the child value set being used in a subsequent presentation of a plurality of value sets to the patient.

40. The system of claim 39, wherein the processor is further configured to: determine whether a value set is included two or more times in a set of child value sets generated in a successive generation; and increase the preference value for a value set if the value set is determined to be included two or more times in a set of child value sets.

41. The system of claim 39, wherein the processor is further configured to increase the preference value for a value set based on the received patient feedback.

42. The system of claim 41, wherein the processor in increasing the preference value for a value set based on the received patient feedback is further configured to increase the preference value for a value set if the patient identifies the value set as a good value set within a specified amount time after presenting the value set to the patient.

43. The system of claim 41, wherein the processor is further configured to: present a value set to the patient based on a receiving a request from the patient to be presented with the value set; and increase the preference value for a value set if the patient identifies the value set as a good value set after being presented with the value set less than a specified number of times.

44. The system of claim 25, wherein the processor is further to: determine whether a specified diversity of the genetic algorithm has been reached; and repeatedly present a plurality of value sets, receive patient feedback, select one or more presented value sets, store information regarding value sets to be excluded, and generate successive generations of value sets until the specified diversity has been reached.

45. The system of claim 44, wherein the processor in determining whether a specified diversity has been reached is configured to determine whether the number of value sets presented to the patient exceeds a threshold.

46. The system of claim 45, wherein the threshold is based on a percentage of possible value sets for the medical implant system.

47. The system of claim 45, wherein the threshold is based on a particular percentage of possible values for one or more of the plurality of fitting parameters included in the value sets.

48. The system of claim 25, wherein the medical implant system is a cochlear implant system and wherein the signals are audible signals.

49. A system for at least partially fitting a medical implant system to a patient comprising:
    means for executing a genetic algorithm to select a determined value set comprising values for a plurality of fitting parameters, the means for executing the genetic algorithm comprising:
        means for presenting signals processed by a plurality of value sets to the patient using the medical implant system;
        means for receiving patient feedback in response to the presented signals processed by the plurality of value sets;
        means for selecting, based on the patient feedback, one or more of the value sets;
        means for storing information, based on patient feedback, regarding one or more value sets that are to be excluded; and
        means for generating one or more successive generations of value sets using said selected one or more value sets; wherein said stored information is used to exclude one or more value sets from said successive generations; and
    means for providing said determined value set to said medical implant system for use in providing stimulation to the patient.

50. A computer-readable medium encoded with instructions operative to cause a computer to perform a method for at least partially fitting a medical implant system to a patient, the method comprising:
    executing a genetic algorithm to select a determined value set comprising values for a plurality of fitting parameters, the genetic algorithm comprising:
        presenting signals processed by a plurality of value sets to the patient using the medical implant system;
        receiving patient feedback in response to the presented signals processed by the plurality of value sets;
        selecting, based on the patient feedback, one or more of the value sets;
        storing information, based on patient feedback, regarding one or more value sets that are to be excluded; and
        generating one or more successive generations of value sets using said selected one or more value sets; wherein said stored information is used to exclude one or more value sets from said successive generations; and
    providing said determined value set to said medical implant system for use in providing stimulation to the patient.

* * * * *